(12) United States Patent
Newman et al.

(10) Patent No.: US 8,383,817 B2
(45) Date of Patent: Feb. 26, 2013

(54) BENZTROPINE COMPOUNDS AND USES THEREOF

(75) Inventors: Amy Hauck Newman, Phoenix, MD (US); Mu-Fa Zou, Baltimore, MD (US); Jonathan L. Katz, Columbia, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 678 days.

(21) Appl. No.: 12/063,072

(22) PCT Filed: Aug. 24, 2006

(86) PCT No.: PCT/US2006/033103
§ 371 (c)(1),
(2), (4) Date: Mar. 11, 2008

(87) PCT Pub. No.: WO2007/025055
PCT Pub. Date: Mar. 1, 2007

(65) Prior Publication Data
US 2008/0226559 A1   Sep. 18, 2008

Related U.S. Application Data

(60) Provisional application No. 60/710,956, filed on Aug. 24, 2005.

(51) Int. Cl.
C07D 451/00 (2006.01)
C07D 451/02 (2006.01)
C07D 43/42 (2006.01)
C07D 451/06 (2006.01)
A61K 31/439 (2006.01)
A61K 31/46 (2006.01)
A61K 31/44 (2006.01)

(52) U.S. Cl. .......... 546/127; 546/129; 514/304
(58) Field of Classification Search .......... None
See application file for complete search history.

(56) References Cited

U.S. PATENT DOCUMENTS

| 2,678,317 | A | 5/1954 | Payne |
|---|---|---|---|
| 5,506,359 | A | 4/1996 | Madras et al. |
| 5,792,775 | A | 8/1998 | Newman et al. |
| 6,395,748 | B2 | 5/2002 | Scheel-Krüger et al. |
| 7,361,667 | B2 | 4/2008 | Zemlan |

FOREIGN PATENT DOCUMENTS

| DE | 1142614 B | * | 1/1963 |
|---|---|---|---|
| WO | WO 94/04146 A1 | | 3/1994 |
| WO | WO 03099783 A2 | * | 12/2003 |
| WO | WO 2004/062610 A2 | | 7/2004 |
| WO | WO 2005/009440 A1 | | 2/2005 |

OTHER PUBLICATIONS

Madras et al. Synapse 29, pp. 93-104 (1998).*
Meltzer et al J Med Chem, pp. 2661-2673 (1997) 40 (17).*
Agoston et al., "Novel N-substituted 3 α-[bis(4'-fluorophenyl)methoxy]tropane analogues: selective ligands for the dopamine transporter," *J. Med. Chem.*, 40, 4329-4339 (1997).
Archer et al., "3α-(Diethylaminoethyl)-aminotropane and Related Compounds," *J. Am. Chem. Soc.*, 79, 4194-4198 (1957).
Bahk et al., "Dopamine D1 and D2 receptor mRNA up-regulation in the caudate-putamen and nucleus accumbens of rat brains by smoking," *Prog. Neuropsychopharmacol. Biol. Psychiatry*, 26, 1095-1104 (2002).
Berdini et al., "A modified palladium catalysed reductive amination procedure," *Tetrahedron*, 58, 5669-5674 (2002).
Brownell et al., "Developments in High-Resolution Positron Emission tomography at MGH," *Intl. J. Imaging Syst. Tech.*, 1, 207-217 (1989).
Brunswick et al., "Greater availability of brain dopamine transporters in major depression shown by [$^{99m}$Tc]TRODAT-1 SPECT imaging," *Am. J. Psychiatry*, 160, 1836-1841 (2003).
Buller et al., "Systemic apomorphine alters HPA axis responses to interleukin-1β administration but not sound stress," *Psychoneuroendocrinology*, 28, 715-732 (2003).

(Continued)

*Primary Examiner* — Kamal Saeed
*Assistant Examiner* — Nyeemah A Grazier
(74) *Attorney, Agent, or Firm* — Leydig, Voit & Mayer, Ltd.

(57) ABSTRACT

Disclosed are benztropine analogs having the formula (I) in which Ar is a $C_6$-$C_{20}$ monocyclic aryl group or a $C_{10}$-$C_{20}$ bicyclic aryl group or a heteroaryl, heterocyclic, or arylheterocyclic group having 2 to 12 carbon atoms and one or more heteroatoms selected from the group consisting of N, O, S, P, and any combination thereof; m=1 to 5; n=1 to 3; and $R^1$ to $R^4$ are as described in the specification; or a pharmaceutically acceptable salt or solvate thereof; pharmaceutical compositions and use thereof, e.g., in treating mental disorders.

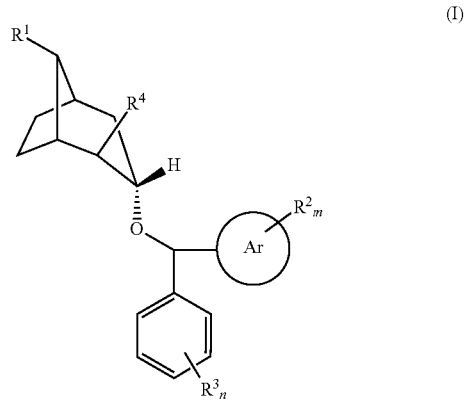

(I)

6 Claims, 14 Drawing Sheets

OTHER PUBLICATIONS

Campbell et al., "Assessment of the influence of histaminergic actions on cocaine-like effects of 3α-diphenylmethoxytropane analogs," 315 (2), 631-640 (2005).

Campiani et al., "Synthesis and pharmacological evaluation of potent and highly selective $D_3$ receptor ligands: inhibition of cocaine-seeking behavior and the role of dopamine $D_3/D_2$ receptors," *J. Med. Chem.*, 46, 3822-3839 (2003).

Carroll, "2002 Medicinal Chemistry Division Award address: monoamine transporters and Opioid receptors. Targets for addiction therapy," *J. Med. Chem.*, 46, 1775-1794 (2003).

Chartoff et al., "Dopamine-dependent increases in phosphorylation of cAMP response element binding protein (CREB) during precipitated morphine withdrawal in primary cultures of rat striatum," *J. Neurochem.*, 87, 107-118 (2003).

Chemical Abstracts, Accession No. 164586 (1994).

Chemical Abstracts, Accession No. 505186 (1985).

Claytor et al., "The Influence of Dopamine D2 and D3 Receptors in Cocaine- and Food-Maintained Responding Under a Second-Order Schedule in Monkeys," *CPDD—2005 Orlando, Florida*, Abstract (Jun. 23, 2005).

Coleman et al., "Single photon emission computed tomography (SPECT). Part II: Clinical applications," *Invest. Radiol.*, 21, 1-11 (1986).

Desai et al., "Identification of a dopamine transporter ligand that blocks the stimulant effects of cocaine," *J. Neurosci.*, 25 (8), 1889-1893 (2005).

Earle et al., "Biochemical screening in the assessment of erectile dysfunction: what tests decide future therapy'?," *Urology*, 62, 727-731 (2003).

Eiler et al., "D1 dopamine receptor regulates alcohol-motivated behaviors in the bed nucleus of the stria terminalis in alcohol-preferring (P) rats," *Synapse*, 489, 45-56 (2003).

Geracioti et al., "Low CSF concentration of a dopamine metabolite in tobacco smokers," *Am. J. Psychiatry*, 156 (1), 130-132 (1999).

Giuliano et al., "Dopamine and Male Sexual Function," *Eur. Urol.*, 40, 601-608 (2001).

Glennon et al., "Synthesis and evaluation of novel alkylpiperazines as potential dopamine antagonists," *J. Med. Chem.*, 24, 678-683 (1981).

Grundt et al., "N-8-Substituted benztropinamine analogs as selective dopamine transporter ligands," *Bioorg. Med. Chem. Ltrs.*, 15, 5419-5423 (2005).

Grundt et al., "The effect of 6-substituted-4',4"-difluorobenztropines on monoamine transporters and the muscarinic M1 receptor," *Bioorg. Med. Chem. Lett.*, 14, 3295-3298 (2004).

Honda et al., "Dopamine $D_3$ agonists into the substantia nigra aggravate cataplexy but do not modify sleep," *NeuroReport.*, 10, 3717-3724 (1999).

Houlihan et al., "Positional Isomer and Analogs of Mazindol as Potential Inhibitors of the Cocaine Binding Site on the Dopamine Transporter Site," *Med. Chem. Res.*, 8:1/2, 77-90 (1998).

Jaszczak et al., "Single photon emission computed tomography (SPECT). Principles and instrumentation," *Invest. Radiol.*, 20, 897-910 (1985).

Jucker et al., "Uber Diarylmethanderivate von 6-Alkoxytropinen," *Helvetica Chimica Acta, XLII* (264), 2451-2457 (1959).

Katz et al., "Dopamine transporter binding without cocaine-like behavioral effects: synthesis and evaluation of benztropine analogs alone and in combination with cocaine in rodents," *Psychopharmacology*, 154, 362-374 (2001).

Kondo et al., "Combination of dopamine $D_2$ receptor gene polymorphisms as a possible predictor of treatment-resistance to dopamine antagonists in schizophrenic patients," *Prog. Neuro-Psychopharmacol. Biol. Psychiatry*, 27, 921-926 (2003).

Kuhar et al., "The dopamine hypothesis of the reinforcing properties of cocaine," *Trends Neurosci.*, 14, 299-302 (1991).

Kulkarni et al., "Structure-activity relationships at monoamine transporters for a series of N-substituted 3α-(bis[4-fluorophenyl]methoxy)tropanes: comparative molecular field analysis, synthesis, and pharmacological evaluation," *J. Med. Chem.*, 47, 3388-3398 (2004).

Laakso et al., "Personality traits and striatal dopamine synthesis capacity in healthy subjects," *Am. J. Psychiatry*, 160 (5), 904-910 (2003).

Lawford et al., "D2 dopamine receptor gene polymorphism: paroxetine and social functioning in posttraumatic stress disorder," *Eur. Neuropsychopharmacol.*, 13, 313-320 (2003).

Lewin et al., "2 β-substituted analogues of cocaine. Synthesis and inhibition of binding to the cocaine receptor," *J. Med. Chem.*, 35, 135-140 (1992).

Martelle et al., "Effects of NMDA antagonists on primary and secondary reinforcing properties of cocaine," *CPDD—2005 Orlando, Florida*, Abstract (Jun. 18, 2005).

Meltzer et al., "2-Carbomethoxy-3-(diarylmethoxy)-1αH, 5αH-tropane analogs: synthesis and inhibition of binding at the dopamine transporter and comparison with piperazines of the GBR series," *J. Med. Chem.*, 39, 371-379 (1996).

Meltzer et al., "Structure-activity-relationships of Inhibition of the Dopamine Transporter by 3-Arylbicyclo[3.2.1]octanes," *Med. Chem. Res.*, 8 (1/2), 12-34 (1998).

Meltzer et al., "The discovery of an unusually selective and novel cocaine analog: difluoropine. Synthesis and inhibition of binding at cocaine recognition sites," *J. Med. Chem.*, 37, 2001-2010 (1994).

Moore, "Organization of midbrain dopamine systems and the pathophysiology of Parkinson's disease," *Parkinsonism Relat. Disord.*, 9 (Suppl. 2), S65-S71 (2003).

Newman et al., "Effects of NMDA antagonists on primary and secondary reinforcing properties of cocaine," *CPDD—2005 Orlando, Florida*, Abstract (Jun. 18, 2005).

Newman et al., "Probes for the dopamine transporter: new leads toward a cocaine-abuse therapeutic—A focus on analogues of benztropine and rimcazole," *Med. Res. Rev.*, 22 (5), 429-464 (2002).

Newman et al., "Structure-activity relationships at monoamine transporters and muscarinic receptors for N-substituted-3α-(3'-chloro-, 4'-chloro-, and 4',4"-dichloro-substituted-diphenyl)methoxytropanes," *J. Med. Chem.*, 44, 633-640 (2001).

Newman, "Novel Dopamine Transporter Ligands: The State of the Art," *Med. Chem. Res.*, 8:1/2, 1-11 (1998).

O'Shea et al., "Is frequent dosing with ecstasy a risky business for dopamine-containing neurons?," *Trends Pharmacol. Sci.*, 24 (6), 272-274 (2003).

Ritz et al., "Cocaine receptors on dopamine transporters are related to self-administration of cocaine," *Science*, 237, 1219-1223 (1987).

Rothman et al., "High affinity dopamine reuptake inhibitors as potential cocaine antagonists: a strategy for drug development," *Life Sci.*, 46, PL-17-PL-21 (1990).

Seeman et al., "Methylphenidate elevates resting dopamine which lowers the impulse-triggered release of dopamine: a hypothesis," *Behav. Brain Res.*, 130, 79-83 (2002).

Singh, "Chemistry, design, and structure-activity relationship of cocaine antagonists," *Chem. Rev.*, 100, 925-1024 (2000).

Solanto, "Dopamine dysfunction in AD/HD: integrating clinical and basic neuroscience research," *Behav. Brain Res.*, 130, 65-71 (2002).

Stocchi et al., "Dual dopamine agonist treatment in Parkinson's disease," *J. Neurol.*, 250, 822-826 (2003).

Swanson et al., "Pharmacokinetic and pharmacodynamic properties of stimulants: implications for the design of new treatments for ADHD," *Behav. Brain Res.*, 130, 73-78 (2002).

Tupala et al., "Dopamine receptors and transporters in the brain reward circuits of type 1 and 2 alcoholics measured with human whole hemisphere autoradiography," *Neuroimage*, 19, 145-155 (2003).

Ukairo et al., "Recognition of benztropine by the dopamine transporter (DAT) differs from that of the classical dopamine uptake inhibitors cocaine, methylphenidate and mazindol as a function of a DAT transmembrane 1 aspartic acid residue," *JPET Fast Forward*, #85829, 1-37 (2005).

Wall et al., "Infralimbic D2 receptor influences on anxiety-like behavior and active memory/attention in CD-1 mice," *Prog. Neuropsychopharmacol. Biol. Psychiatry*, 27, 395-410 (2003).

Wisor et al., "Dopaminergic role in stimulant-induced wakefulness," *J. Neurosci.*, 21 (5), 1787-1794 (2001).

Xu et al., "Synthesis and biological evaluation of 2-substituted 3β-tolyltropane derivatives at dopamine, serotonin, and norepinephrine transporters," *J. Med. Chem.*, 45, 1203-1210 (2002).

Young et al., "Dopamine transporter polymorphism associated with externalizing behavior problems in children," *Am. J. Med. Genet.*, 114, 144-149 (2002).

Zou et al., "Enantioselective synthesis of S-(+)-2β-carboalkoxy-3α-[bis(4-fluorophenyl)methoxy]tropanes as novel probes for the dopamine transporter," *Bioorganic & Medicinal Chemistry Letters*, 12, 1249-1252 (2002).

Zou et al., "Structure-activity relationship comparison of (S)-2?-substituted 3a-(bis[4-fluorophenyl]methoxy)tropanes and (R)-2/?-substituted 3/?-(3,4-dichlorophenyl)tropanes at the dopamine transporter," *J. Med. Chem.*, 46, 2908-2916 (2003).

Zou et al., "Synthesis and binding profile of a novel series of (S)-2β-substituted-4',4''-difluorobenztrophine analogs," *230th ACS National Meeting*, Washington, DC (2005).

European Patent Office Communication pursuant to Article 94(3) EPC, Application No. 06 789 971.6; dated Oct. 31, 2008.

International Preliminary Report on Patentability, Application No. PCT/US2006/033103, dated Feb. 26, 2008.

Kline et al., "3'-Chloro-3α-(diphenylmethoxy)tropane But Not 4'-chloro-3α(diphenylmethoxy)tropane Produces a Cocaine-like Behavioral Profile," *J. Med. Chem.*, 40 (6), 851-857 (1997).

\* cited by examiner

FIG. 1A
FIG. 1B
FIG. 1C
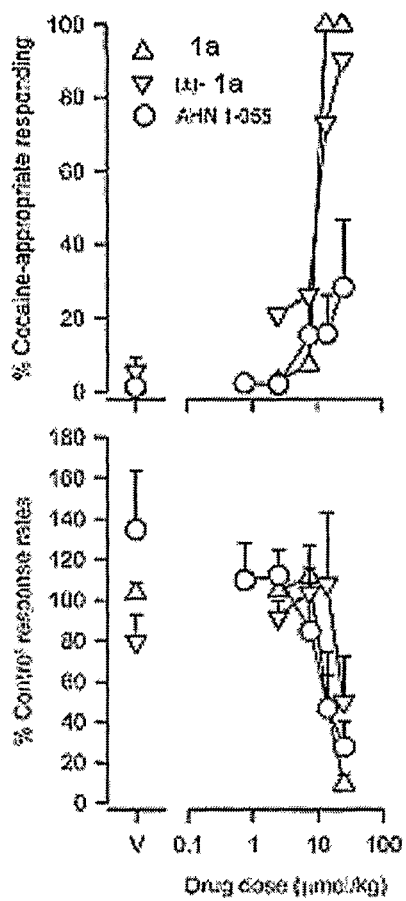
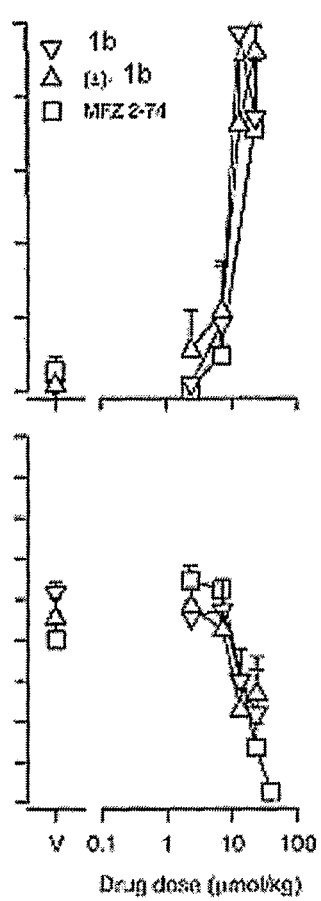
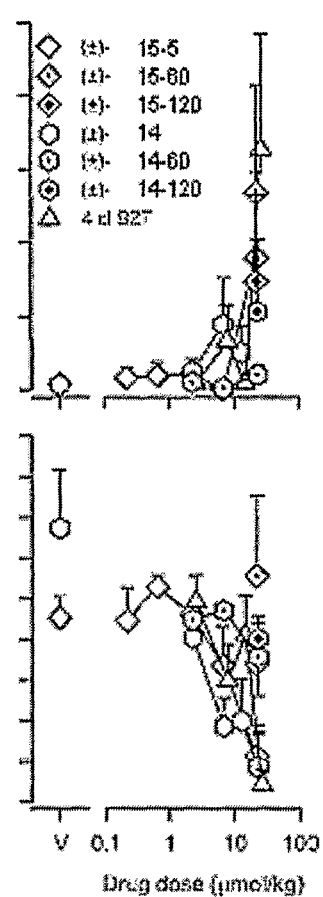
FIG. 1D
FIG. 1E
FIG. 1F

1a

BENZTROPINE COMPOUNDS AND USES THEREOF

BACKGROUND OF THE INVENTION

The present invention relates generally to a family of benztropine compounds or tropane analogs, pharmaceutical compositions comprising them, and their use to treat various diseases or conditions including mental disorders.

The significant public health and social problems resulting from cocaine abuse have stimulated research efforts directed toward elucidating the central mechanisms by which cocaine exerts its behavioral effects. The data from these studies suggest that the primary mechanism of the behavioral effects of cocaine appears to be related to the inhibition of dopamine uptake (see, Ritz, M. C., et al., *Science*, 237, 1219-1223 (1987); and Kuhar, M. J., et al., *Trends Neurosci.*, 14, 299-301 (1991)) which results in an elevated concentration of dopamine in the synapse. As a consequence, considerable emphasis has been directed toward the dopamine transporter as a target for research and potential therapeutics for the treatment of cocaine abuse.

There have been several approaches to finding tropane analogs as potential medications for psychostimulant abuse and other mental disorders; see, for example, Singh, S., *Chem. Rev.*, 100, 925-1024 (2000); Newman A. H. and Kulkarni S. S., *Med. Res. Rev.*, 22, 429-464 (2002); Newman, A. H., *Med. Chem. Res.*, 8, 1-11 (1998); Carroll, F. I., *J. Med. Chem.*, 46, 1775-1794 (2003), Agoston et al., *J. Med. Chem.*, 40, 4329-39 (1997); Desai et al., *J. Neurosci.*, 25, 1889-93 (Feb. 23, 2005); Kulkarni et al., *J. Med. Chem.*, 47, 3388-98 (2004); Xu et al., *J. Med. Chem.*, 45, 1203-10 (2002); Zou et al., *Bioorg. Med. Chem. Lett.*, 12, 1249-52 (2002); Zou et al., *J. Med. Chem.*, 46, 2908-16 (2003); and U.S. Pat. No. 5,792,775. Although some of the reported analogs have demonstrated some cocaine-like discriminative stimulus effects, there remains a need for tropane or benztropine analogs which have affinity for the dopamine transporter but without a significant behavioral profile of cocaine. The present invention provides such analogs. This and other objects and advantages of the invention, as well as additional inventive features will be apparent from the description of the invention provided herein.

BRIEF SUMMARY OF THE INVENTION

The foregoing need has been fulfilled by the present invention which provides a family of tropane analogs. Particularly, the present invention provides a family of benztropine analogs having the Formula I:

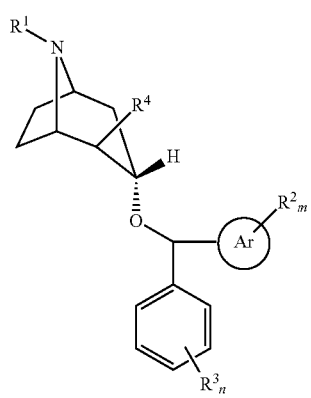

(I)

in which $R^1$ is selected from the group consisting of hydrogen, $C_1$-$C_{12}$ alkyl, $C_2$-$C_{12}$ alkenyl, $C_2$-$C_{12}$ alkynyl, $C_6$-$C_{20}$ aryl $C_1$-$C_{12}$ alkyl, $C_5$-$C_{20}$ heteroaryl $C_1$-$C_{12}$ alkyl, $C_1$-$C_{12}$ aminoalkyl, $C_1$-$C_{12}$ alkoxy $C_1$-$C_{12}$ alkyl, $C_5$-$C_{20}$ heterocycloalkyl $C_1$-$C_{12}$ alkyl, $C_1$-$C_{12}$ alkylsulfonyl, $C_2$-$C_{12}$ alkylcarbonyl, $(N(C_6$-$C_{20}$ aryl)amido)$C_1$-$C_{12}$ alkyl, $(N(C_1$-$C_{12}$ alkyl)amido)$C_1$-$C_2$ alkyl, $(N(C_6$-$C_{20}$ aryl)amido)$C_2$-$C_{12}$ alkylcarbonyl, $(N(C_1$-$C_{12}$ alkyl)amido)$C_2$-$C_{12}$ alkylcarbonyl, $C_1$-$C_{12}$ alkylamido $C_6$-$C_{20}$ aryl, and a polymer; m=1 to 5; n=1 to 3; $R^2$ and $R^3$ are each independently selected from the group consisting of hydrogen, halo, $C_1$-$C_{12}$ alkyl, $C_1$-$C_{12}$ alkoxy, nitro, cyanato, isocyanato, thiocyanato, amino, halo $C_1$-$C_{12}$ alkyl, hydroxyl, trihalo $C_1$-$C_{12}$ alkyl, and any combination thereof; $R^4$ is selected from the group consisting of hydroxyl, carboxyl, $C_1$-$C_{12}$ alkyl, $C_1$-$C_{12}$ alkoxy, $C_2$-$C_{12}$ carboxyalkyl, $C_2$-$C_{12}$ alkylcarbonyl, $C_2$-$C_{12}$ alkyloxycarbonyl, $C_6$-$C_{20}$ aryl oxycarbonyl, $C_6$-$C_{20}$ aryl $C_2$-$C_{12}$ alkyloxycarbonyl, $C_2$-$C_{12}$ alkyloxycarbonyl $C_1$-$C_{12}$ alkyl, $C_6$-$C_{20}$ aryl, $C_6$-$C_{20}$ aryl $C_2$-$C_{12}$ alkylcarbonyloxy $C_1$-$C_{12}$ alkyl, $C_1$-$C_{12}$ alkylsulfonyl, $C_1$-$C_{12}$ hydroxyalkyl, formyl, $C_2$-$C_{12}$ formylalkyl, $C_2$-$C_{12}$ alkenyl, $C_2$-$C_{12}$ alkyloxycarbonyl $C_2$-$C_{12}$ alkenyl, and $C_2$-$C_{12}$ alkynyl; Ar is a $C_6$-$C_{20}$ monocyclic aryl group or a $C_{10}$-$C_{20}$ bicyclic aryl group or a heteroaryl, heterocyclic, or aryl heterocyclic group having 2 to 12 carbon atoms and one or more heteroatoms selected from the group consisting of N, O, S, P, and any combination thereof, and wherein any of $R^1$, $R^2$, $R^3$, and $R^4$ other than hydrogen, halo, hydroxyl, nitro, cyanato, isocyanato, and thiocyanato can be further substituted with one or more substituents selected from the group consisting of halo, hydroxyl, cyanato, isocyanato, thiocyanato, amino, $C_1$-$C_{12}$ alkyl, amido, nitro, methoxy, $CF_3$, azido, $C_2$-$C_{12}$ alkylcarbonyl, amino, $C_1$-$C_{12}$ alkylamino, $C_2$-$C_{12}$ alkylcarbonyl, and any combination thereof; or a pharmaceutically acceptable salt or solvate thereof.

The benztropine analogs of the present invention have an affinity for the dopamine transporter and inhibit dopamine uptake, but they do not produce a significant stimulation of locomotor activity or cocaine-like subjective effects in a drug discrimination model. The benztropine analogs have one or more advantageous properties, e.g., improved water solubility, increased stability, and/or selectivity.

The benztropine analogs of the present invention find use as therapeutics, e.g., cocaine antagonists or cocaine substitutes, for the treatment of cocaine abuse. The present invention also provides methods of treating a patient for a mental disorder.

The present invention further provides a method of administering a benztropine compound of Formula III

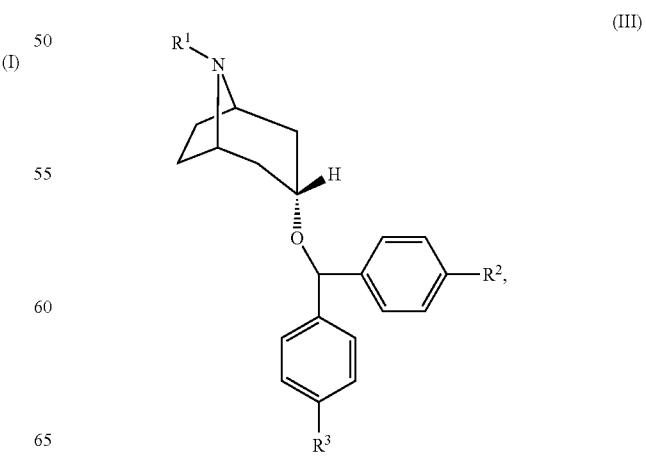

(III)

in which $R^1$-$R^3$ are as described herein, to a mammal to increase attention to relevant signals (stimuli) in the environment relative to an untreated control, reduce the effect of nicotine by at least 50%, and/or reduce food intake.

The benztropine analogs of the present invention find use as imaging probes for dopamine transporter/cocaine binding sites and as imaging probes for neurodegenerative disorders (e.g., Parkinson's disease). The present invention also provides a method of selectively imaging cocaine binding sites of the central nervous system of a human patient, the method comprising administering to the central nervous system of the patient a compound described above and detecting the binding of that compound to the central nervous system tissue.

The present invention also provides a method of detecting or monitoring Parkinsonism in a patient, the method comprising administering to the patient a detectably labeled compound described above and detecting the binding of that compound to the central nervous system tissue. Using this method, one can diagnose and/or monitor Parkinson's disease, a neurological disorder characterized by the progressive degeneration of dopamine nerve terminals.

BRIEF DESCRIPTION OF THE SEVERAL VIEWS OF THE DRAWINGS

FIG. 1 (A-F) illustrates the effects of 2-substituted BZT analogues in rats measured as (i) a percentage of responses on the cocaine-appropriate lever (A, B, and C) or (ii) rates at which responses were emitted as a percentage of responses after saline administration (D, E, and F) versus drug dose (μmol/kg) (log scale).

FIG. 2 graphically illustrates locomotor activity counts after drug administration versus time since injection and placement of subject in the experimental chamber. Each point represents the average effect determined in six to eight mice, for successive 10-min time periods up to 480 min (8 h) after injection. FIG. 2A represents injection of 1a.

FIG. 3 graphically illustrates specific [$^{125}$I]RTI-121 binding as a percentage of that obtained after vehicle injection versus time. For each point the number of replicates was from 5 to 10. FIG. 3A represents injection of 1a.

DETAILED DESCRIPTION OF THE INVENTION

Figure 2A:
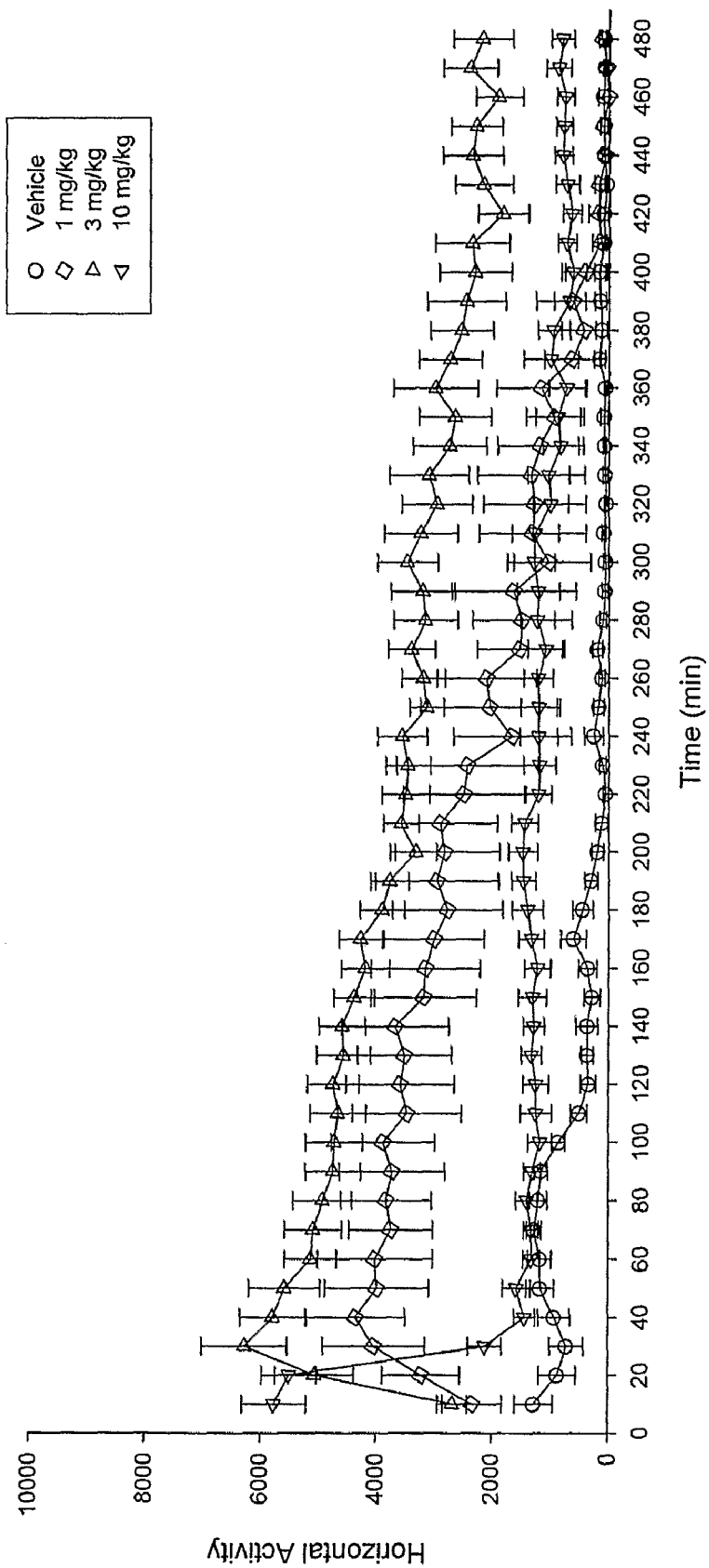

In one aspect, the present invention provides compounds having the general Formula I:

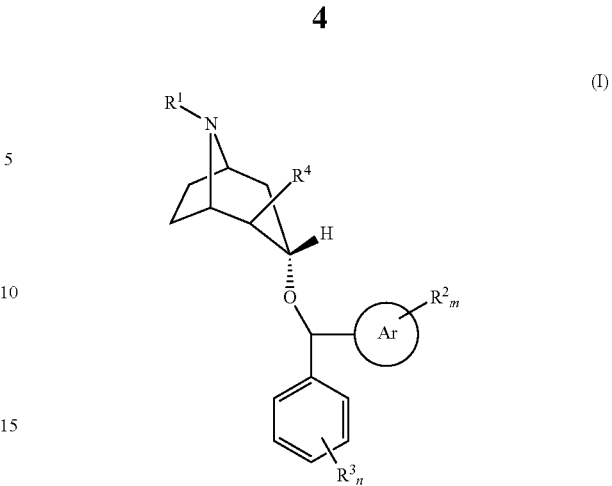

or a pharmaceutically acceptable salt or solvate thereof.

In Formula I, $R^1$ is selected from the group consisting of hydrogen, $C_1$-$C_{12}$ alkyl, $C_2$-$C_{12}$ alkenyl, $C_2$-$C_{12}$ alkynyl, $C_6$-$C_{20}$ aryl $C_1$-$C_{12}$ alkyl, $C_5$-$C_{20}$ heteroaryl $C_1$-$C_{12}$ alkyl, $C_1$-$C_{12}$ aminoalkyl, $C_1$-$C_{12}$ alkoxy $C_1$-$C_{12}$ alkyl, $C_5$-$C_{20}$ heterocycloalkyl $C_1$-$C_{12}$ alkyl, $C_1$-$C_{12}$ alkylsulfonyl, $C_2$-$C_{12}$ alkylcarbonyl, (N($C_6$-$C_{20}$ aryl)amido)$C_1$-$C_{12}$ alkyl, (N($C_1$-$C_{12}$ alkyl)amido)$C_1$-$C_{12}$ alkyl, (N($C_6$-$C_{20}$ aryl)amido)$C_2$-$C_{12}$ alkylcarbonyl, (N($C_1$-$C_{12}$ alkyl)amido)$C_2$-$C_{12}$ alkylcarbonyl, $C_1$-$C_{12}$ allylamido $C_6$-$C_{20}$ aryl, and a polymer. The polymer can be any pharmaceutically acceptable polymer. Preferably, the polymer is one that will not decrease the solubility of the compound, such as a hydrophilic polymer, for example, polyalkylene glycols such as polyethylene glycol, dextrans, polyglutamates, polylactides, and the like. Typically, $R^1$ is selected from the group consisting of hydrogen, $C_1$-$C_{12}$ alkyl, $C_2$-$C_{12}$ alkenyl, $C_6$-$C_{20}$ aryl-$C_1$-$C_{12}$ alkyl, $C_1$-$C_{12}$ aminoalkyl, $C_5$-$C_{20}$ heterocycloalkyl-$C_1$-$C_{12}$ alkyl, and (N($C_6$-$C_{20}$-aryl)amido)$C_1$-$C_{12}$ alkyl. Preferably, $R^1$ is selected from the group consisting of hydrogen, $C_1$-$C_6$ alkyl, $C_2$-$C_6$ alkenyl, $C_6$-$C_{10}$ aryl-$C_1$-$C_6$ alkyl, $C_1$-$C_6$ aminoalkyl, $C_5$-$C_{10}$ heterocycloalkyl-$C_1$-$C_6$ alkyl, and (N($C_6$-$C_{10}$-aryl)amido)$C_1$-$C_6$ alkyl. More preferably, $R^1$ is selected from the group consisting of methyl, ethyl, propyl, butyl, allyl, phenylbutyl, 2-aminoethyl, [2-(1H-indol-3-yl)-ethyl]-, and 3-[(N-phenyl)amidopropyl].

The group Ar in Formula I is a $C_6$-$C_{20}$ monocyclic aryl group, a $C_{10}$-$C_{20}$ bicyclic aryl group, or a heteroaryl group, heterocyclic, or arylheterocyclic group having 2 to 12 carbon atoms and one or more heteroatoms selected from the group consisting of N, O, S, P, and any combination thereof. Typically Ar is selected from the group consisting of phenyl, naphthyl, biphenyl, pyridyl, bipyridyl, pyrimidyl, pyrrolyl, furanyl, thiophenyl, triazolyl, triazolopyrimidyl, thiadiazolyl, phosphole, diazaphosphole, quinoxalyl, benzofuranyl, benzopyrrolyl, morpholinyl, benzopyranyl, oxolyl, thiazolyl, purinyl, imidazolyl, indolyl, phosphindolyl ($C_8H_6P$—), pyrazolyl, and isoindolyl. Preferably, Ar is phenyl or naphthyl. More preferably, Ar is phenyl.

$R^2$ and $R^3$ are each independently selected from the group consisting of hydrogen, halo, $C_1$-$C_{12}$ alkyl, $C_1$-$C_{12}$ alkoxy, nitro, cyanato, isocyanato, thiocyanato, amino, halo $C_1$-$C_{12}$ alkyl, hydroxyl, trihalo $C_1$-$C_{12}$ alkyl, and any combination thereof. Typically, $R^2$ and $R^3$ are selected from the group consisting of hydrogen, halo, $C_1$-$C_6$ alkyl, $C_1$-$C_6$ alkoxy, nitro, cyanato, isocyanato, thiocyanato, amino, halo $C_1$-$C_6$ alkyl, hydroxyl, trihalo $C_1$-$C_6$ alkyl, and any combination thereof. Preferably $R^2$ is fluoro, chloro, or hydrogen and/or $R^3$ is fluoro or chloro. More preferably, $R^2$ and $R^3$ are fluoro.

The number of groups $R^2$ (m) and $R^3$ (n) present in Formula I is m=1 to 5 and n=1 to 3, respectively. In some embodiments, the phenyl and Ar rings each can have only one substituent such that m=n=1. In other embodiments, the phenyl ring can have one or two substituents (n is 1 or 2) while the Ar ring(s) can have 1 to 5 substituents (m=1 to 5). $R^2$ and $R^3$ can occupy any suitable position. Preferably $R^2$ and $R^3$ do not occupy a position that is ortho to the methylene linkage, e.g., they occupy meta- and/or para-positions.

$R^4$ is selected from the group consisting of hydroxyl, carboxyl, $C_1$-$C_{12}$ alkyl, $C_1$-$C_{12}$ alkoxy, $C_2$-$C_{12}$ carboxyalkyl, $C_2$-$C_{12}$ alkylcarbonyl, $C_2$-$C_{12}$ alkyloxycarbonyl, $C_6$-$C_{20}$ aryl oxycarbonyl, $C_6$-$C_{20}$ aryl $C_2$-$C_{12}$ alkyloxycarbonyl, $C_2$-$C_{12}$ alkyloxycarbonyl $C_1$-$C_{12}$ alkyl, $C_6$-$C_{20}$ aryl, $C_6$-$C_{20}$ aryl $C_2$-$C_{12}$ alkylcarbonyloxy $C_1$-$C_{12}$ alkyl, $C_1$-$C_{12}$ alkylsulfonyl, $C_1$-$C_{12}$ hydroxyalkyl, formyl, $C_2$-$C_{12}$ formylalkyl, $C_2$-$C_{12}$ alkenyl, $C_2$-$C_{12}$ alkyloxycarbonyl $C_2$-$C_{12}$ alkenyl, and $C_2$-$C_{12}$ alkynyl. In some embodiments, $R^4$ desirably is selected from the group consisting of hydroxyl, carboxyl, $C_1$-$C_{12}$ alkyl, $C_1$-$C_{12}$ alkoxy, $C_2$-$C_{12}$ carboxyalkyl, $C_2$-$C_{12}$ alkyloxycarbonyl $C_1$-$C_{12}$ alkyl, $C_6$-$C_{20}$ aryl, $C_6$-$C_{20}$ aryl $C_2$-$C_{12}$ alkylcarbonyloxy $C_1$-$C_{12}$ alkyl, $C_1$-$C_{12}$ alkylsulfonyl, $C_1$-$C_{12}$ hydroxyalkyl, formyl, $C_2$-$C_{12}$ formylalkyl, $C_2$-$C_{12}$ alkenyl, $C_2$-$C_{12}$ alkyloxycarbonyl $C_2$-$C_{12}$ alkenyl, and $C_2$-$C_{12}$ alkynyl. In other embodiments, $R^4$ desirably is selected from the group consisting of $C_2$-$C_{12}$ alkylcarbonyl, $C_2$-$C_{12}$ alkyloxycarbonyl, $C_5$-$C_{20}$ aryloxycarbonyl, and $C_6$-$C_{20}$ aryl $C_2$-$C_{12}$ alkyloxycarbonyl. Typically $R^4$ is selected from the group consisting of hydroxyl, carboxyl, $C_1$-$C_6$ alkyl, $C_1$-$C_6$ alkoxy, $C_2$-$C_6$ carboxyalkyl, $C_2$-$C_6$ alkylcarbonyl, $C_2$-$C_6$ alkyloxycarbonyl, $C_6$-$C_{10}$ aryloxycarbonyl, $C_6$-$C_{10}$ aryl $C_2$-$C_6$ alkyloxycarbonyl, $C_2$-$C_6$ allyloxycarbonyl $C_1$-$C_6$ alkyl, $C_6$-$C_{10}$ aryl, $C_6$-$C_{10}$ aryl $C_2$-$C_6$ alkylcarbonyloxy $C_1$-$C_6$ alkyl, $C_1$-$C_6$ alkylsulfonyl, $C_1$-$C_6$ hydroxyalkyl, formyl, $C_2$-$C_6$ formylalkyl, $C_2$-$C_6$ alkenyl, $C_2$-$C_6$ alkyloxycarbonyl $C_2$-$C_6$ alkenyl, and $C_2$-$C_6$ alkynyl. Preferably $R^4$ is selected from the group consisting of methyloxycarbonyl, ethyloxycarbonyl, hydroxymethyl, formyl, methyloxycarbonylethenyl, methyloxycarbonylethyl, ethenyl, 4-nitrophenylpropylcarbonyloxyethyl, and 4-aminophenylpropylcarbonyloxyethyl. More preferably $R^4$ is selected from the group consisting of ethenyl, hydroxymethyl, methyloxycarbonylethenyl, and methyloxycarbonylethyl.

Any of the groups $R^1$, $R^2$, $R^3$, and $R^4$, other than hydrogen, halo, hydroxyl, nitro, cyanato, isocyanato, and thiocyanato can be further substituted with one or more substituents selected from the group consisting of halo, hydroxyl, cyanato, isocyanato, thiocyanato, amino, $C_1$-$C_{12}$ alkyl, amido, nitro, methoxy, $CF_3$, azido, $C_2$-$C_{12}$ alkylcarbonyl, amino, $C_1$-$C_{12}$ alkylamino, $C_2$-$C_{12}$ alkylcarbonyl, and any combination thereof.

The term "independently selected" is used herein to indicate that the two R groups, i.e., $R^2$ and $R^3$, can be identical or different (e.g., $R^2$ and $R^3$ may both be methoxy), two or more $R^2$ groups can be identical or different, or two or more $R^3$ groups can be identical or different.

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p. 1445, and *Journal of Pharmaceutical Science*, 66, 2-19 (1977).

Suitable bases include inorganic bases such as alkali and alkaline earth metal bases, e.g., those containing metallic cations such as sodium, potassium, magnesium, calcium and the like. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, fatty acids, long chain fatty acids, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, hydrobromide, iodide, acetate, propionate, caprate, caprylate, acrylate, ascorbate, formate, hydrochloride, dihydrochloride, isobutyrate, caproate, heptanoate, propiolate, glucuronate, glutamate, propionate, phenylpropionate, salicylate, oxalate, malonate, succinate, suberate, sebacate, fumarate, malate, maleate, hydroxymaleate, behenate, oleate, mandelate, nicotinate, isonicotinate, cinnamate, hippurate, nitrate, stearate, phthalate, terephthalate, butylyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, hydroxybutyrate, glycolate, tartrate, hemi-tartrate, benzenesulfonate, methanesulfonate, ethanesulfonate, propanesulfonate, hydroxyethanesulfonate, 1-naphthalenesulfonate, 2-napththalenesulfonate, 1,5-naphthalenedisulfonate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid. Preferred pharmaceutically acceptable salts are hydrochloride, hydrobromide, oxalate, maleate, methanesulfonate, and hemi-tartrate. A particularly preferred pharmaceutically acceptable salt is hydrochloride. The compounds of the present invention are useful in the form of the free base or acid or in the form of a pharmaceutically acceptable salt thereof.

It should be recognized that the particular counter ion forming a part of any salt of this invention is usually not of a critical nature, so long as the salt as a whole is pharmacologically acceptable and as long as the counter ion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

Within the scope of Formula I, certain embodiments are preferred, for example, when the substituent $R^4$ is in the E-position as shown in Formula II.

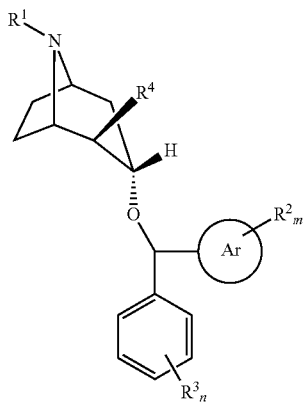

(II)

For example, preferred compounds include those of Formula I or II in which $R^1$ is selected from the group consisting of hydrogen, $C_1$-$C_{12}$ alkyl, $C_2$-$C_{12}$ alkenyl, $C_6$-$C_{20}$ aryl-$C_1$-$C_{12}$ alkyl, $C_1$-$C_{12}$ aminoalkyl, $C_5$-$C_{20}$ heterocycloalkyl-$C_1$-$C_{12}$ alkyl, and (N($C_6$-$C_{20}$-aryl)amido)$C_1$-$C_{12}$ alkyl; m=n=1; Ar is phenyl; $R^2$ and $R^3$ are halo; and $R^4$ is methyloxycarbonyl, ethyloxycarbonyl, hydroxymethyl, formyl, methyloxycarbonylethenyl, methyloxycarbonylethyl, ethenyl, 4-nitrophenylpropylcarbonyloxyethyl, or 4-aminophenylpropylcarbonyloxyethyl. In some embodiments, $R^1$ is selected from the group consisting of hydrogen, $C_1$-$C_6$ alkyl, $C_2$-$C_6$ alkenyl, $C_6$-$C_{10}$ aryl-$C_1$-$C_6$ alkyl, $C_1$-$C_6$ aminoalkyl, $C_5$-$C_{10}$ heterocycloalkyl-$C_1$-$C_6$ alkyl, and (N($C_6$-$C_{10}$-aryl)amido)$C_1$-$C_6$ alkyl; m=n=1; Ar is phenyl; $R^2$ and $R^3$ are halo; and $R^4$ is methyloxycarbonyl, ethyloxycarbonyl, hydroxymethyl, formyl, methyloxycarbonylethenyl, methyloxycarbonylethyl, ethenyl, 4-nitrophenylpropylcarbonyloxyethyl, or 4-aminophenylpropylcarbonyloxyethyl. Also preferred are compounds in which $R^1$ is selected from the group consisting of methyl, n-butyl, allyl, phenylbutyl, 2-aminoethyl, [2-(1H-indol-3-yl)-ethyl]-, and 3-[(N-phenyl)amidopropyl]; m=n=1; Ar is phenyl; $R^2$ and $R^3$ are halo; and $R^4$ is methyloxycarbonyl, ethyloxycarbonyl, hydroxymethyl, formyl, methyloxycarbonylethenyl, methyloxycarbonylethyl, ethenyl, 4-nitrophenylpropylcarbonyloxyethyl, or 4-aminophenylpropylcarbonyloxyethyl.

In some embodiments of Formula I or II, $R^1$ is selected from the group consisting of hydrogen, $C_1$-$C_{12}$ alkyl, $C_2$-$C_{12}$ alkenyl, $C_6$-$C_{20}$ aryl-$C_1$-$C_{12}$ alkyl, $C_1$-$C_{12}$ aminoalkyl, $C_5$-$C_{20}$ heterocycloalkyl-$C_1$-$C_{12}$ alkyl, and (N($C_6$-$C_{20}$-aryl)amido)$C_1$-$C_{12}$ alkyl; m=n=1; Ar is phenyl; $R^2$ and $R^3$ are chloro or fluoro; and $R^4$ is methyloxycarbonyl, ethyloxycarbonyl, hydroxymethyl, formyl, methyloxycarbonylethenyl, methyloxycarbonylethyl, ethenyl, 4-nitrophenylpropylcarbonyloxyethyl, or 4-aminophenylpropylcarbonyloxyethyl; specifically $R^1$ is selected from the group consisting of hydrogen, $C_1$-$C_{12}$ alkyl, $C_2$-$C_{12}$ alkenyl, $C_6$-$C_{20}$ aryl-$C_1$-$C_{12}$ allyl, $C_1$-$C_{12}$ aminoalkyl, $C_5$-$C_{20}$ heterocycloalkyl-$C_1$-$C_{12}$ alkyl, and (N($C_6$-$C_{20}$-aryl)amido)$C_1$-$C_{12}$ alkyl; m=n=1; Ar is phenyl; $R^2$ and $R^3$ are 4-chloro or 4-fluoro; and $R^4$ is methyloxycarbonyl, ethyloxycarbonyl, hydroxymethyl, formyl, methyloxycarbonylethenyl, methyloxycarbonylethyl, ethenyl, 4-nitrophenylpropylcarbonyloxyethyl, or 4-aminophenylpropylcarbonyloxyethyl; and particularly $R^1$ is selected from the group consisting of hydrogen, $C_1$-$C_{12}$ alkyl, $C_2$-$C_{12}$ alkenyl, $C_6$-$C_{20}$ aryl-$C_1$-$C_{12}$ alkyl, $C_1$-$C_{12}$ aminoalkyl, $C_5$-$C_{20}$ heterocycloalkyl-$C_1$-$C_{12}$ alkyl, and (N($C_6$-$C_{20}$-aryl)amido)$C_1$-$C_{12}$ alkyl; m=n=1; Ar is phenyl; $R^2$ and $R^3$ are 4-chloro or 4-fluoro; and $R^4$ is methyloxycarbonyl or ethyloxycarbonyl. More particularly preferred compounds are selected from the group consisting of:

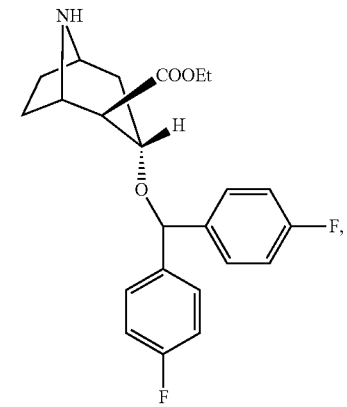

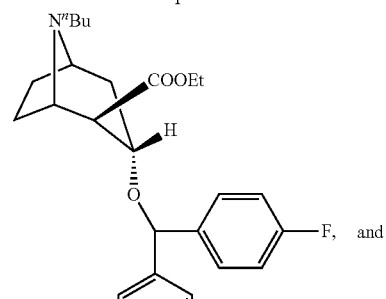

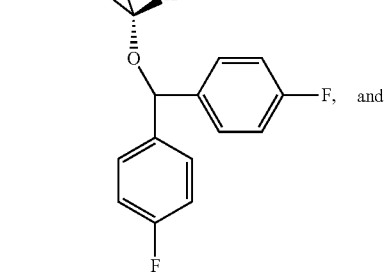

In other embodiments of Formula I or II, m=n=1; Ar is phenyl; $R^1$ is selected from the group consisting of hydrogen, methyl, n-butyl, allyl, phenylbutyl, 2-aminoethyl, [2-(1H-indol-3-yl)-ethyl]-, and 3-[(N-phenyl)amidopropyl]; $R^2$ and $R^3$ are 4-fluoro or 4-chloro; and $R^4$ is hydroxymethyl, formyl, methyloxycarbonylethenyl, methyloxycarbonylethyl, ethenyl, 4-nitrophenylpropylcarbonyloxyethyl, or 4-aminophenylpropylcarbonyloxyethyl; specifically m=n=1; Ar is phenyl; $R^1$ is methyl; $R^2$ and $R^3$ are 4-fluoro or 4-chloro; and $R^4$ is hydroxymethyl, formyl, methyloxycarbonylethenyl, methyloxycarbonylethyl, ethenyl, 4-nitrophenylpropylcarbonyloxyethyl, or 4-aminophenylpropylcarbonyloxyethyl. More particularly preferred compounds are selected from the group consisting of:

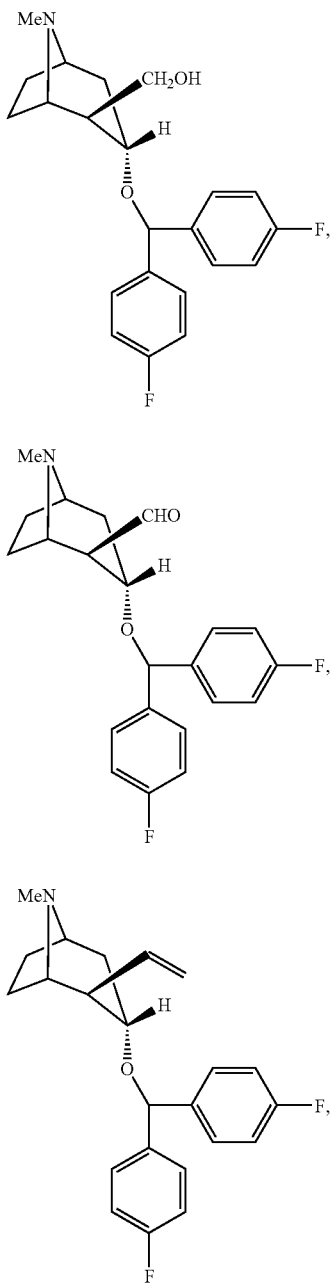
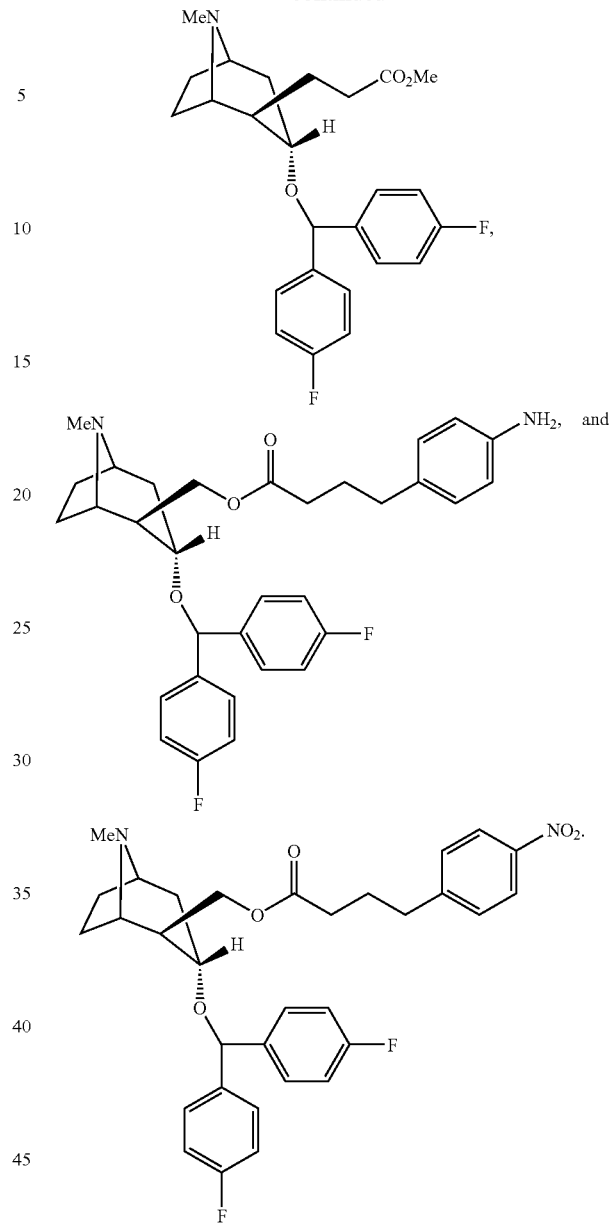

In yet other embodiments of Formula I or II, m=n=1; Ar is phenyl; $R^1$ is selected from the group consisting of hydrogen, methyl, ethyl, 2-propyl, $(CH_2)_pCH_3$, $CH_2CF_3$, $CH_2(CH_2)_pOH$, $CH_2(CH_2)_p$—O—$(CH_2)_qCH_3$, $CH_2CH$=$CHX$, 2-(1-piperidinyl)ethyl, 2-(4-morpholinyl)ethyl, and $(CH_2)_pC_6H_4X$, wherein X is selected from the group consisting of H, halo, hydroxyl, methoxy, $CF_3$, nitro, amino, cyanato, $NHCOCH_3$, $N(CH_3)_2$, $(CH_2)_pCH_3$, azido, $C(O)CH_3$, and $C(CH_3)_3$; p=0-6; q=0-4; $R^4$ is selected from the group consisting of $C_2$-$C_{12}$ alkylcarbonyl, $C_2$-$C_{12}$ alkyloxycarbonyl, $C_5$-$C_{20}$ aryloxycarbonyl, and $C_6$-$C_{20}$ aryl $C_2$-$C_{12}$ alkyloxycarbonyl; and at least one of $R^2$ and $R^3$ is selected from the group consisting of $C_1$-$C_{12}$ alkyl, $C_2$-$C_{12}$ alkoxy, nitro, cyanato, isocyanato, thiocyanato, amino, halo $C_1$-$C_{12}$ alkyl, and trihalo $C_1$-$C_{12}$ alkyl.

It should be noted, however, that for compounds of Formula II, if Ar is phenyl, m=n=1, $R^1$ is $CH_3$, and $R^4$ is $COOCH_3$, both $R^2$ and $R^3$ are not simultaneously hydrogen, 4-halo or 4-methyl. In addition, if Ar is phenyl, m=n=1, $R^1$ is $CH_3$, and $R^1$ and $R^3$ are 4-fluoro, $R^4$ is not $COOC_2H_5$, $CO_2CH(CH_3)_2$, $CO_2CH_2Ph$, $CO_2CH_2CH_2Ph$, $CO_2CH_2CH_2Ph$-4'-$NO_2$, $CO_2CH_2CH_2Ph$-4'-$NH_2$, $CO_2CH_2CH_2Ph$-3'-I, 4'-$NH_2$, $CO_2CH_2CH_2Ph$-3'-I, 4'-$N_3$, or $CO_2CH_2CH_2Ph$-4'-NCS. Also, if Ar is phenyl, m=n=1, $R^1$ is $CH_3$, $R^4$ is $COOCH_3$, and $R^2$ is hydrogen, $R^3$ is not 4-halo or 4-methyl, or alternatively if Ar is phenyl, m=n=1, $R^1$ is $CH_3$, $R^4$ is $COOCH_3$, and $R^2$ is 4-bromo, $R^3$ is not 4-iodo. Moreover, if Ar is phenyl, m=1, n=2, $R^1$ is $CH_3$, $R^4$ is $COOCH_3$, and $R^2$ is hydrogen, $R^3$ is not hydroxyl, 2-propoxyl, alkoxyl, or methylcarbonyloxy.

The compounds of Formula I or II can be prepared by any suitable method, for example, by using the synthetic schemes set forth in Schemes 1-3. As shown in Scheme 1, a (S)-2β-carboalkoxybenztropine compound is reduced to form the corresponding (S)-2β-alcohol. A subsequent Swern oxidation of the (S)-2β-alcohol compound provides the corresponding (S)-2β-aldehyde analog. A Wittig reaction of the (S)-2β-aldehyde compound with methyltriphenylphosphonium bromide gives the (S)-2β-alkene analog. Alternatively, Musamune-Rousch olefination of the (S)-2β-aldehyde with trimethylphosphonoacetate produces the (S)-2β-unsaturated ester. Catalytic hydrogenation of the (S)-2β-unsaturated ester gives the (S)-2β-saturated ester compound.

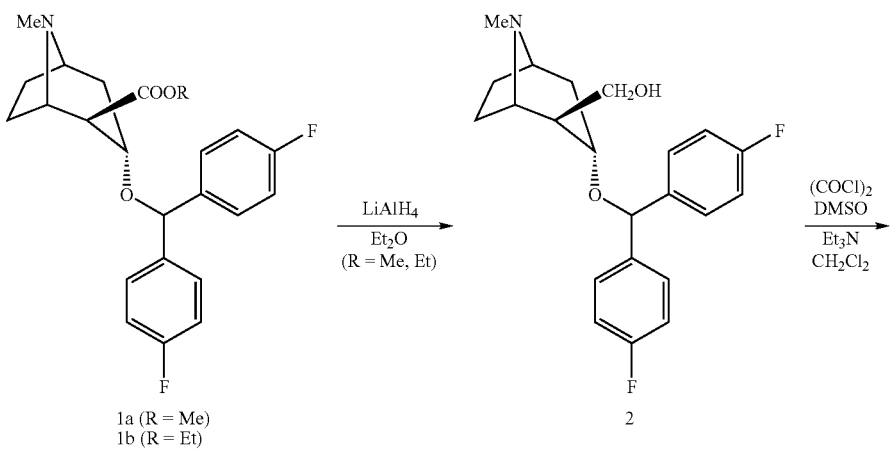

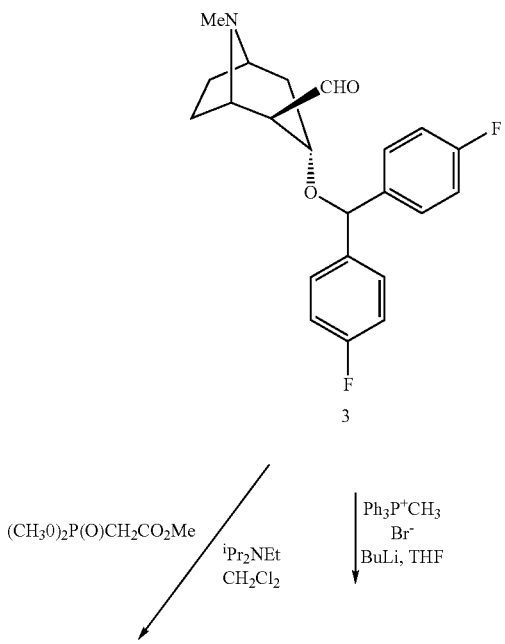

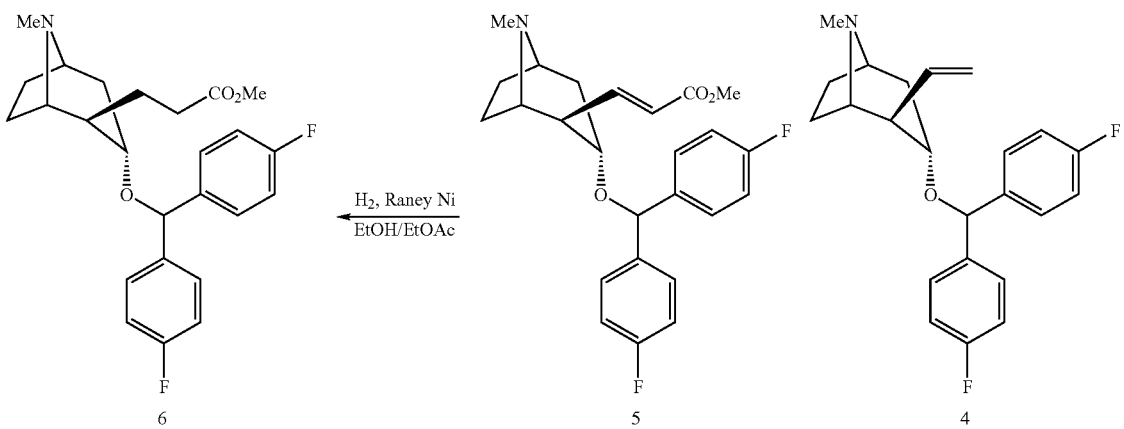

As shown in Scheme 2, the (S)-2β-alcohol compound can also be reacted with 4-(p-nitrophenyl)butyric acid chloride to produce the (S)-2β-methyl-4-(p-nitrophenyl)butyric acid ester compound. Subsequent reduction of the nitro group with Raney Ni produces the aniline analog.

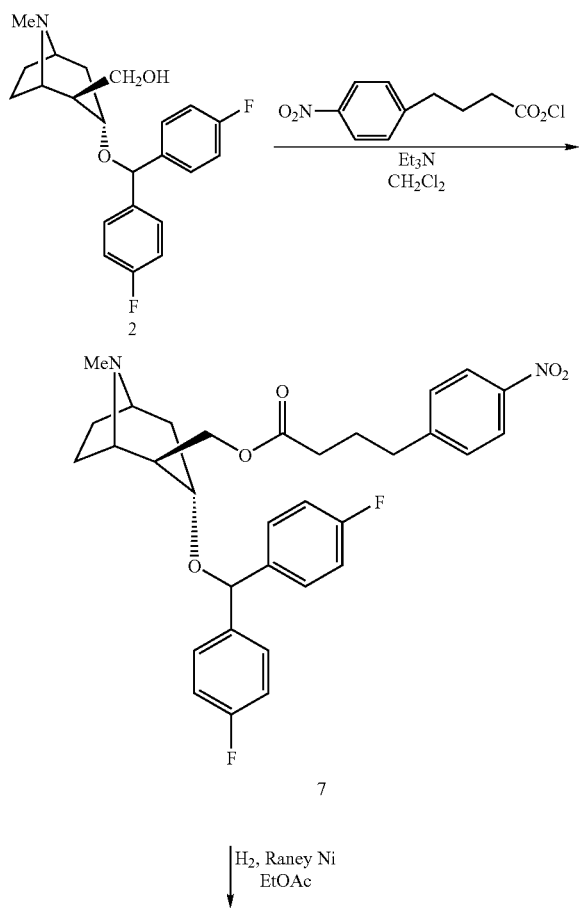

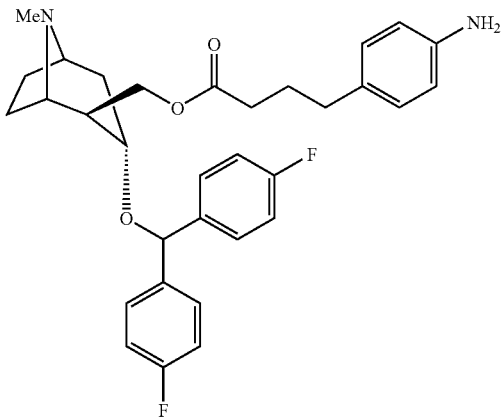

It will be readily apparent to those of skill in the art that the N-methyl group on the tropane can be substituted with other functional groups using standard chemical reactions known to them. For example, the N-methyl group can be replaced with other functional groups including, but not limited to, hydrogen, $C_1$-$C_{12}$ alkyl, $C_2$-$C_{12}$ alkenyl, $C_2$-$C_2$ alkynyl, $C_6$-$C_{20}$ aryl $C_1$-$C_{12}$ alkyl, $C_5$-$C_{20}$ heteroaryl $C_1$-$C_{12}$ alkyl, $C_1$-$C_{12}$ alkylamino, $C_5$-$C_{20}$ heterocycloalkyl $C_1$-$C_{12}$ alkyl, $C_1$-$C_{12}$ alkylsulfonyl, $C_2$-$C_{12}$ alkylcarbonyl, (N($C_6$-$C_{20}$ aryl) amido)$C_1$-$C_{12}$ alkyl, (N($C_1$-$C_{12}$ alkyl)amido)$C_1$-$C_{12}$ alkyl, and a polymer. Alternatively, alkylation can occur upon reaction with the appropriate acid in the presence of DCC (dicyclohexylcarbodiimide) and HOBt (1-hydroxybenzotriazole hydrate). For example, the functional group $R^4$=[2-(1H-indol-3-yl)-ethyl]- can be obtained by reaction with 2-indoleacetic acid. In particular as shown in Scheme 3, the benztropine nitrogen of the (S)-2β-carboalkoxybenztropine compound can be modified by demethylation reaction following the Oloffson procedure. The N-allyl and N-butyl compounds are generated by subsequent reaction with allyl bromide and butyl bromide, respectively.

Scheme 3

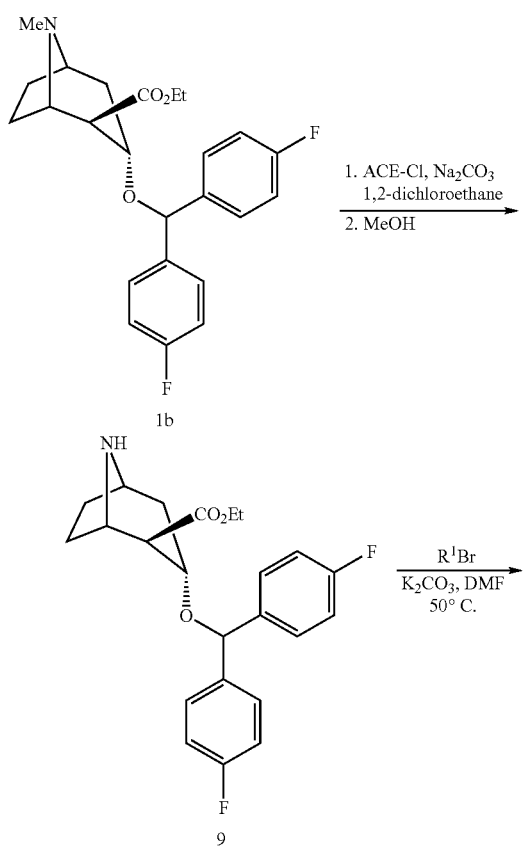

In order to understand the neurochemical and behavioral properties of the compounds of the present invention, exemplary benztropine analogs were evaluated for displacement of [$^3$H]WIN 35,428 (2β-carbomethoxy-3β-(4-fluorophenyl)tropane) binding to the DAT in rat caudate-putamen. These benztropine analogs were also evaluated for displacement of radiolabeled ligand binding at the serotonin (SERT) and norepinephrine (NET) transporters as well as the muscarinic $m_1$ receptor (M1), Tables 1 and 2, infra. The NET over DAT selectivity refers to the ratio of respective $K_i$ values. When the $K_i$ ratio is greater than 1, the compound is DAT selective. The DAT selectivities of the analogs over these binding sites are depicted in Table 3.

TABLE 1

Inhibition constants ($K_i$) at the monoamine transporters and the muscarinic M1 receptor in rat brain membranes[a]

| Compound | $R^1$ | $R^4$ | DAT [$^3$H]WIN 35,428 $K_i$ ± SEM (nM) | SERT [$^3$H]citalopram $K_i$ ± SEM (nM) | NET [$^3$H]nisoxetine $K_i$ ± SEM (nM) | $M_1$ [$^3$H]pirenzepine $K_i$ ± SEM (nM) |
|---|---|---|---|---|---|---|
| 1a | CH$_3$ | COOCH$_3$ | 2.94 ± 0.36 | 689 ± 58.4 | 269 ± 38.9[b] | 133 ± 4.16 |
| 2 | CH$_3$ | CH$_2$OH | 3.52 ± 0.42 | 910 ± 65 | 983 ± 97.0 | 109 ± 15.1 |
| 4 | CH$_3$ | CH=CH$_2$ | 1.81 ± 0.21 | 1790 ± 114 | 473 ± 64.2 | 163 ± 23.1 |
| 5 | CH$_3$ | CH=CHCO$_2$CH$_3$ | 4.69 ± 0.60 | 572 ± 51 | 269 ± 34.8 | 1380 ± 81.0 |
| 6 | CH$_3$ | CH$_2$CH$_2$CO$_2$CH$_3$ | 3.74 ± 0.07 | 1070 ± 118 | 454 ± 43.2 | 3110 ± 435 |
| 7 | CH$_3$ | CH$_2$OCO(CH$_2$)$_3$C$_6$H$_4$NO$_2$-p | 39.9 ± 4.31 | 3780 ± 390 | 2130 ± 157 | 708 ± 102 |
| 8 | CH$_3$ | CH$_2$OCO(CH$_2$)$_3$C$_6$H$_4$NH$_2$-p | 27.6 ± 0.85 | 1390 ± 145 | 440 ± 17.7 | 342 ± 33.7 |
| 1b | CH$_3$ | COOCH$_2$CH$_3$ | 6.87 ± 0.33 | 1850 ± 270 | 629 ± 31[b] | 1890 ± 132 |
| 9 | H | COOCH$_2$CH$_3$ | 8.87 ± 1.02 | 2150 ± 222 | 563 ± 73.9 | 17100 ± 2480 |

TABLE 1-continued

Inhibition constants ($K_i$) at the monoamine transporters and the muscarinic M1 receptor in rat brain membranes[a]

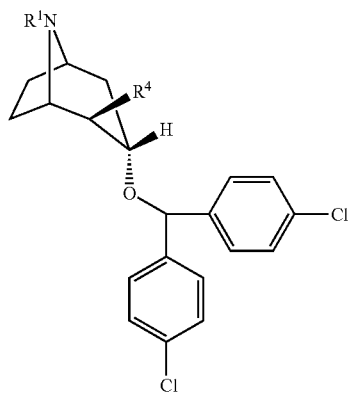

| Compound | $R^1$ | $R^4$ | DAT [³H]WIN 35,428 $K_i$ ± SEM (nM) | SERT [³H]citalopram $K_i$ ± SEM (nM) | NET [³H]nisoxetine $K_i$ ± SEM (nM) | $M_1$ [³H]pirenzepine $K_i$ ± SEM (nM) |
|---|---|---|---|---|---|---|
| 10 | butyl | COOCH₂CH₃ | 8.18 ± 0.17 | 2500 ± 327 | 580 ± 15.9 | 3200 ± 298 |
| 11 | allyl | COOCH₂CH₃ | 11.0 ± 0.94 | 2280 ± 125 | 935 ± 113 | 11400 ± 1650 |
| 12[c] | butyl | H | 9.70 ± 0.91 | 1350 ± 151 | 1490 ± 190 | 399 ± 26.8 |
| 13[c] | allyl | H | 8.79 ± 0.52 | 2850 ± 62.5 | 1570 ± 242 | 177 ± 21.1 |

[a]Each $K_i$ value represents data from at least three independent experiments, each performed in triplicate. $K_i$ values were analyzed by PRISM. The binding assay methods were conducted as reported previously (see Kulkarni S., J. Med. Chem., 47, 3388-98 (2004)) except that the DAT assay was run in sucrose buffer.
[b]Incubation time was 1 h; for all others incubation time was 3 h.
[c]Comparative data taken from Agoston et al. (J. Med. Chem., 40, 4329-39 (1997))

TABLE 2

Binding data for (S) and (±)-2-substituted 3α-[bis(4-chlorophenyl)methoxy]tropanes.

| Compound | $R^1$ | $R^4$ | DAT binding $K_i^{a,b}$ (nM) | DA uptake $IC_{50}^{a,b}$ (nM) | SERT $K_i^{a,b}$ (nM) | NET $K_i^{a,b}$ (nM) | $M_1$ $K_i^{a,b}$ (nM) |
|---|---|---|---|---|---|---|---|
| S-14 | CH₃ | COOCH₃ | 12.6 ± 0.40 | 2.46 ± 0.2 | 528 ± 39 | 2150 ± 325 | 382 ± 37 |
| (±)-14 | CH₃ | COOCH₃ | 23.4 ± 1.5 | NT | NT | NT | NT |
| S-15 | CH₃ | COOCH₂CH₃ | 14.6 ± 0.39 | 1.52 ± 0.2 | 1560 ± 91 | 3350 ± 154 | 3060 ± 150 |
| (±)-15 | CH₃ | COOCH₂CH₃ | 22.0 ± 0.84 | NT | NT | NT | NT |
| 4,4-diCl BZT[d] | CH₃ | H | 17.5 ± 0.88[e] | 23.4 ± 3.0[c] | 1640 ± 236[c] | 2980 ± 182[c] | 40.6 ± 8.0[c] |

[a]Each $K_i$ value represents data from at least three independent experiments, each performed in triplicate. $K_i$ values were analyzed by PRISM.
[b]Binding methods were conducted as previously reported ((Katz et al., Psychopharmacology, 154, 362-374 (2001) and Kulkarni et al., J. Med. Chem., 47, 3388-3398 (2004)) except that the DAT assay was run in sucrose buffer.
[c]Data from Katz et al., Psychopharmacology, 154, 362-374 (2001) and included for reference.
[d]3α-(bis-Cl-phenylmethoxy)tropane.
[e]The $K_i$ values for these compounds at DAT were assessed using different methods (Katz et al., Psychopharmacology, 154, 362-374 (2001) and Kulkarni et al., J. Med. Chem., 47, 3388-3398 (2004)) than those used for the other compounds. In our experience the values obtained using those methods give $K_i$ values that are approximately three-fold higher than those obtained with the methods used for the other compounds.
NT = not tested.

TABLE 3

Binding selectivities for the benztropine analogs

| Compound | DAT/SERT | DAT/NET | DAT/M$_1$ |
|---|---|---|---|
| 1a | 234 | 91 | 45 |
| 2 | 258 | 279 | 31 |
| 4 | 989 | 261 | 90 |
| 5 | 115 | 54 | 278 |
| 6 | 286 | 121 | 831 |
| 7 | 94 | 53 | 18 |
| 8 | 50 | 16 | 12 |
| 1b | 269 | 91 | 275 |
| 9 | 242 | 63 | 1928 |
| 10 | 305 | 71 | 391 |
| 11 | 207 | 85 | 1036 |
| 12 | 139 | 153 | 41 |
| 13 | 324 | 178 | 20 |

All of the compounds displaced [$^3$H]WIN 35,428 binding at the dopamine transporter with high affinity (K$_i$ =1.81 to 39.9 nM). The most potent compound in this exemplary series is compound 4, K$_i$=1.81 nM. None of these compounds demonstrate high affinity to the NET, SERT or muscarinic M1 receptors. All compounds showed high selectivity in binding to the DAT over SERT, NET and muscarinic M1 receptor except for compounds 7 and 8, which showed reduced DAT/M1 selectivity. Compound 9 is the most DAT/M1 selective benztropine compound reported to date.

A comparison between compound 1a and compounds 5 and 6 reveals that increasing the chain length at the 2-position does not significantly affect binding affinity to the DAT (2.94 nM v. 4.96 nM and 3.74 nM, respectively). N-Demethylation to the N-nor analog and substitution with N-n-butyl or N-allyl slightly decreases binding affinity to the DAT compared to the parent compounds 1a and 1b. Conversely, addition of the 2β-COOEt to compounds 12 or 13 had no effect on DAT binding but significantly improved DAT/M1 selectivity.

The benztropine analogs of the present invention find use as therapeutics for the treatment of a mental disorders, e.g., those selected from the group consisting of conduct disorders, alcohol addiction, tobacco addiction, nicotine addiction, drug addiction, sleep disorders, obesity by reducing food intake, inhalation disorders, Parkinsonism including Parkinson's disease, female and male orgasmic disorders, female and male sexual arousal disorders, hypoactive sexual desire disorder, and anxiety, stress and/or depression disorders. Preferably, the benztropine analogs are used to treat cocaine abuse, narcolepsy or cataplexy, obesity by reducing food intake, tobacco addiction, nicotine addiction, or Attention Deficit Hyperactivity Disorder (ADHD). More preferably, the benztropine analogs are used to treat cocaine abuse.

In an embodiment of the inventive method, in particular, treatment of ADHD, obesity by reducing food intake, tobacco addiction, and/or nicotine addiction, the compound of Formula I or II has m=n=1; Ar is phenyl; R$^1$ is selected from the group consisting of hydrogen, C$_1$-C$_{12}$ alkyl (e.g., methyl, ethyl, 2-propyl), (CH$_2$)$_p$CH$_3$, CH$_2$CF$_3$, CH$_2$(CH$_2$)$_p$OH, CH$_2$(CH$_2$)$_p$—O—(CH$_2$)$_q$CH$_3$, CH$_2$CH=CHX, 2-(1-piperidinyl)ethyl, 2-(4-morpholinyl)ethyl, and (CH$_2$)$_p$C$_6$H$_4$X, wherein X is selected from the group consisting of H, halo, hydroxyl, methoxy, CF$_3$, nitro, amino, cyanato, NHCOCH$_3$, N(CH$_3$)$_2$, (CH$_2$)$_p$CH$_3$, azido, C(O)CH$_3$, and C(CH$_3$)$_3$; p=0-6; q=0-4; R$^4$ is selected from the group consisting of C$_2$-C$_{12}$ alkylcarbonyl, C$_2$-C$_{12}$ alkyloxycarbonyl, C$_5$-C$_{20}$ aryloxycarbonyl, and C$_6$-C$_{20}$ aryl C$_2$-C$_{12}$ alkyloxycarbonyl; and at least one of R$^2$ and R$^3$ is selected from the group consisting of C$_1$-C$_{12}$ alkyl, C$_2$-C$_{12}$ alkoxy, nitro, cyanato, isocyanato, thiocyanato, amino, halo, halo C$_1$-C$_{12}$ alkyl, and trihalo C$_1$-C$_{12}$ alkyl. Preferably, the compound of Formula I or II used in the inventive method has m=n=1; Ar is phenyl; R$^1$ is selected from the group consisting of C$_1$-C$_{12}$ alkyl (e.g., methyl); R$^4$ is C$_2$-C$_{12}$ alkyloxycarbonyl (e.g., methyloxycarbonyl, ethyloxycarbonyl; i-propyloxycarbonyl); and R$^2$ and R$^3$ are the same or different and each is selected from hydrogen and halo (e.g., F, Cl).

These compounds inhibit dopamine uptake and provide elevated levels of extracellular dopamine that alleviate the symptoms of cocaine abstinence (see, Rothman, R. B., et al., *Life Sci. Pharmacol. Lett.* 1990, 46, PL-17-PL-21) in a manner similar to the way in which the nicotine patch or nicotine chewing gum protects against withdrawal symptoms after cessation of tobacco use. Further, as a result of their lack of cocaine-like behavioral effects, these compounds are not subject to abuse themselves. Thus, the benztropine analogs of the present invention can serve to keep drug abusers from seeking cocaine, but they will not become substitute addictive drugs.

As used herein, "cocaine abuse" has its conventional meaning, i.e., misuse or addiction of cocaine. Conventional thought suggests that cocaine is taken by a person due to a craving for cocaine generated by its prior use. Excessive use of cocaine produces many serious and adverse side effects. As such, it is highly desirable to reduce the number and/or intensity of episodes of cocaine abuse. Abstinence from cocaine is thought to be associated with decreased dopamine levels in the brain that result in feelings of dysphoria. If dopamine levels remain elevated, the dysphoria will be prevented, and the individual will not seek cocaine. As such, compounds that increase dopamine levels for a prolonged period of time (without causing euphoria and reinforcement that would lead to their abuse) would provide a therapeutic treatment for cocaine addiction.

The ability of these compounds to inhibit dopamine uptake and likewise cause increased and sustained dopamine levels in the brain is also useful for treating other addiction and mental disorders including alcohol addiction (see Eiler et al., *Synapse*, 489, 45 (2003); Tupala et al., *Neuroimage*, 19, 145 (2003)), nicotine addiction (see Bahk et al., *Prog. Neuropsychopharmacol. Biol. Psychiatry*, 26, 1095 (2002); Geracioti et al., *Am. J. Psychiatiy*, 156, 130 (1999)); other types of drug addiction (see Campiani et al., *J. Med. Chem.*, 46, 3822 (2003); Chartoff et al., *J. Neurochem.*, 38, 107 (2003); O'Shea et al., *Trends Pharmacol. Sci.*, 24, 272 (2003)); obesity (by reducing food intake) (see U.S. Pat. No. 6,395,748); sexual dysfunction including orgasmic disorder, female/male sexual arousal disorders, and hypoactive sexual desire disorder (see Earler et al., *Urology*, 62, 727 (2003); Guiliano et al., *Eur. Urol.*, 40, 601 (2001)); sleep disorders including narcolepsy and cataplexy (see Wisor et al., *J. Neurosci.*, 21, 1787 (2001); Honda et al., *Neuroreport*, 10, 3713 (1999)); Parkinsonism including Parkinson's disease (see Moore, *Parkinsonism Relat. Disord.*, 9 Suppl. 2, S65 (2003); Stocchi et al., *J. Neurol.*, 250, 822 (2003)); conduct disorders including ADHD (see Young et al., *Am. J. Med. Genet.*, 114, 144 (2002); Seeman et al., *Behav. Brain Res.*, 130, 79 (2002); Solanto, *Behav. Brain Res.*, 130, 65 (2002); Swanson et al., *Behav. Brain Res.*, 130, 73 (2002)); and depression, anxiety, and stress disorders (see Wall et al., *Prog. Neuropsychopharmacol. Biol. Psychiatiy*, 27, 395 (2003); Laasko et al., *Am. J. Psychiatry*, 160, 904 (2003); Lawford et al., *Eur. Neuropsychopharinacol.*, 13, 313 (2003); Buller et al., *Psychoneuroen-* docrinology, 28, 715 (2003); Brunswick et al., *Am. J. Psychiatiy*, 160, 1836 (2003); Kondo et al., *Prog. Neuropsychopharmacol. Biol. Psychiatry*, 27, 921 (2003).

In a further embodiment, the present invention provides a method of increasing attention to stimuli in the environment relative to an untreated control in a mammal comprising administering to the mammal an effective amount of a benztropine compound of the formula (III):

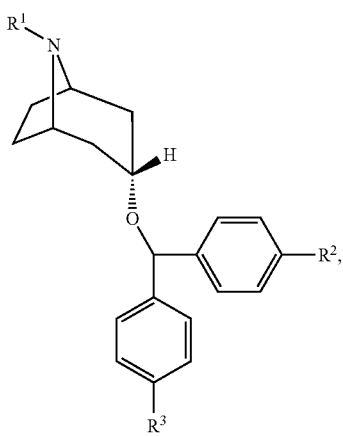

in which $R^1$ is $C_1$-$C_2$ alkyl or $C_2$-$C_{12}$ alkenyl; and $R^2$ and $R^3$ are each independently hydrogen or halo. Such method is useful in the treatment of ADHD. Preferably, $R^1$ is methyl and $R^2$ and $R^3$ are fluoro.

Also provided is a method of reducing the effect of nicotine by at least 50% in a mammal comprising administering to the mammal an effective amount of a benztropine compound of the formula (III):

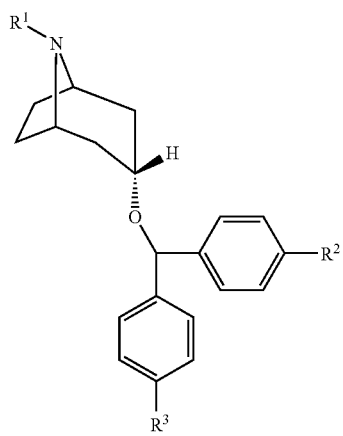

in which $R^1$ is $C_1$-$C_{12}$ alkyl or $C_2$-$C_{12}$ alkenyl; and $R^2$ and $R^3$ are each independently hydrogen or halo. Such method is useful for treating nicotine and/or tobacco addiction. Preferably, $R^1$ is methyl, allyl, or butyl, and $R^2$ and $R^3$ are fluoro.

In yet another embodiment, the invention provides a method of reducing food intake in a mammal comprising administering to the mammal an effective amount of a benztropine compound of the formula (III):

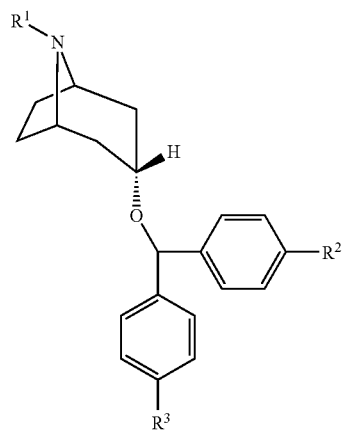

in which $R^1$ is $C_1$-$C_2$ allyl or $C_2$-$C_{12}$ alkenyl; and $R^2$ and $R^3$ are each independently hydrogen or halo. Such method is useful in the treatment of weight disorders, including obesity. Preferably, (a) $R^1$ is methyl, allyl, or butyl, and $R^2$ and $R^3$ are fluoro; or (b) $R^1$ is methyl, $R^2$ is chloro, and $R^3$ is hydrogen.

The benztropine compounds of Formula III can be prepared by any suitable method, for example, by using the synthetic schemes set forth in U.S. Pat. No. 5,792,775.

In another aspect, the present invention provides a method of treating a patient for a mental disorder, the method comprising administering to the patient a therapeutically effective amount of a compound of Formula I-III. It will be appreciated that the compositions and methods of the invention do not require that the compound of Formula I be present in an enantiomerically pure form (i.e., all compounds having the substituent $R^4$ in the β-position), rather the compositions and methods of the invention can comprise the compound of Formula I in racemic form. Preferably, the compound of Formula II or III is present in at least about 5% ee, about 10% ee, about 20% ee, about 30% ee, about 40% ee, about 50% ee, about 60% ee, about 70% ee, about 80% ee, about 90% ee, or about 100% ee.

"Treatment" or "treating," as used herein, refer to any administration of a compound of the present invention and include: (i) inhibiting the symptoms of the mental disorder, e.g., cocaine addiction; and/or (ii) lessening or inhibiting the long term effects of the mental disorder, e.g., cocaine addiction. In therapeutic applications, compositions are administered to a patient already suffering from the mental disorder, e.g., cocaine addiction, in an amount sufficient to cure or at least partially arrest or alleviate the symptoms of the mental disorder and/or its complications. An amount adequate to accomplish this is defined as a "therapeutically effective" amount or dose. Amounts effective for this use will depend on the severity and course of the mental disorder, previous therapy, the patient's health status and response to the drugs, and the judgment of the treating physician.

In conjunction with the foregoing method, the present invention provides pharmaceutical compositions comprising a compound of any of Formula I-III and a pharmaceutically acceptable carrier, diluent, or excipient. The phrase "pharmaceutically or therapeutically acceptable carrier," as used herein, refers to a carrier medium which does not interfere with the effectiveness of the biological activity of the active ingredients and which is not toxic to the host or patient. The pharmaceutical compositions of the present invention can be in a variety of forms. These include, for example, solid, semi-solid and liquid dosage forms, such as tablets, pills, powders, liquid solutions or suspensions, liposomes, injectable and infusible solutions. Inhalable preparations, such as aerosols, are also included. Preferred formulations are those directed to oral, intranasal and parenteral applications, but it will be appreciated that the preferred form will depend on the particular therapeutic application at hand. The methods for the formulation and preparation of therapeutic compositions comprising the compounds of the invention are well known in the art and are described in, for example, REMINGTON'S PHARMACEUTICAL SCIENCES (Mack Publishing Company, Philadelphia, Pa., 17th ed. (1985)), THE MERCK INDEX 11th Ed., (Merck & Co. 1989), and Langer, *Science*, 249, 1527-1533 (1990).

The pharmaceutical compositions containing the compounds of the present invention can be administered for therapeutic and/or prophylactic treatments. In therapeutic applications, compositions are administered to a patient already suffering from a mental disorder, e.g., cocaine addiction or Parkinson's disease, in an amount sufficient to cure or at least partially arrest the symptoms of the mental disorder and its complications.

In prophylactic applications, the pharmaceutical compositions are administered to a patient susceptible to or otherwise at risk for a particular disease in an amount sufficient to prevent or ameliorate the onset of symptoms. Such an amount is defined as a "prophylactically effective amount or dose." These can be administered orally or by inhalation. In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the mental disorder symptoms.

In general, a suitable effective dose of the compounds of the present invention will be in the range of 0.05 to 1000 milligram (mg) per recipient per day, preferably in the range of 0.1 to 100 mg per day. The desired dosage is preferably presented in one, two, three, four or more subdoses administered at appropriate intervals throughout the day. These subdoses can be administered as unit dosage forms, for example, containing 0.01 to 1000 mg, preferably 0.01 to 100 mg of active ingredient per unit dosage form. Again, the desired dosage will depend on, for example, the particular compound employed, the mental disorder to be treated, the manner of administration, the weight and general state of health of the patient, and the judgment of the prescribing physician.

While it is possible to administer the active ingredient of this invention alone, it is preferable to present it as part of a pharmaceutical formulation. The formulations of the present invention comprise at least one compound described herein in a therapeutically or pharmaceutically effective dose together with a pharmaceutically acceptable carrier. For parenteral administration, for example, the pharmaceutical compositions comprise a solution of a compound of Formula I, as described above, dissolved or suspended in an acceptable carrier, preferably an aqueous carrier. A variety of aqueous carriers can be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally about 10% to about 95% of the active ingredient and, more preferably, about 25% to about 75% of the active ingredient.

For aerosol administration, the compounds of Formula I-V are preferably supplied in a finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included as desired, as with, e.g., lecithin, for intranasal delivery.

In addition to the foregoing, the benztropine analogs of the present invention are useful as imaging probes for dopamine transporter/cocaine binding sites and as imaging probes for neurodegenerative disorders (e.g., Parkinson's disease). As such, in another aspect, the present invention provides a method of selectively imaging cocaine binding sites of the central nervous system of a human, the method comprising: (a) administering to the central nervous system of the patient a compound having the Formula I; and (b) detecting the binding of that compound to the central nervous system tissue.

In yet another aspect, the present invention provides a method of detecting or monitoring Parkinsonism in a patient, the method comprising: (a) administering to the human a detectably labeled compound having the Formula I; and (b) detecting the binding of that compound to the central nervous system tissue. Using this method, one can diagnose and/or monitor Parkinson's disease, a neurological disorder characterized by the progressive degeneration of dopamine nerve terminals.

The previous discussion pertaining to various embodiments including preferred embodiments of benztropine analogs as compounds per se is applicable to the benztropine analogs used in the method of imaging cocaine binding sites and in the methods of diagnosing/monitoring Parkinsonism and, thus, they will not be repeated herein. In an embodiment, the benztropine analogs of the present invention are labeled with a radioactive or fluorescent label using standard labeling techniques known to and used by those of skill in the art. Suitable labels include, but are not limited to $^{11}$C on the N-linked $R^1$ substituent; $^{123}$I, $^{76}$Br or $^{18}$F, in an embodiment, on the phenylarylmethyl group attached to O; and $^{99}$Tc on the phenylarylmethyl group attached to O.

In addition, in an embodiment, binding of the benztropine analogs to the CNS tissue is detected using positron emission tomography (PET) or single-photon emission computed tomography (SPECT). PET imaging may be carried using any appropriate apparatus, but is preferably carried out using coded single ring positron tomograph (Brownell et al., *Intl. J. Imaging Syst. Tech.*, 1, 207-217, 1989). The analog ring design offers a number of advantages for positron tomography. PET imaging can be carried out on conscious human subjects. In addition, SPECT imaging may also be used on human subjects (See, e.g., Medicine, *Scientific American, Inc.*, ed. Rubenstein and Federman, 1988; Jaszczak and Coleman, *Invest. Radiol.*, 20, 897, 1985; and Coleman, et al., *Invest. Radiol.*, 21, 1, 1986); preferably SPECT imaging employs gamma-emitting derivatives of the analogs described herein (e.g., benztropine analogs labeled with $^{123}$I or $^{99}$Tc).

As such, using the benztropine analogs of the present invention, one can (1) assay cocaine receptors in chronic cocaine users and in individuals exposed to cocaine prenatally, (2) assay the receptor occupancy of potential cocaine therapeutics, (3) assay cocaine receptors in individuals that abuse other drugs, (4) investigate the mechanism by which cocaine and related drugs alter behavior, (5) elucidate the receptor properties of the dopamine transporter receptor complex, (6) study the mechanism of dopamine transport, etc. Thus, the benztropine analogs of the present invention are useful, inter alia, in research, e.g., in in vivo and in vitro experiments, to study dopamine transport, the dopamine transport receptor and, in particular, cocaine binding sites.

The invention will be described in greater detail by way of specific examples. The following examples are offered for illustrative purposes, and are intended neither to limit nor define the invention in any manner.

EXAMPLES

General Methodology. All chemicals and reagents were purchased from Aldrich Chemical Co. or Lancaster Synthesis, Inc., and used without further purification. All melting points were determined on a Thomas-Hoover melting point apparatus and are uncorrected. The $^1$H and $^{13}$C NMR spectra were recorded on Bruker AC-300 or a Varian Mercury Plus 400 instruments. Proton chemical shifts are reported as parts per million (δ ppm) relative to tetramethylsilane (0.00 ppm) as an internal standard. Coupling constants are measured in Hertz. Chemical shifts for $^{13}$C NMR spectra are reported as δ relative to deuterated chloroform (CDCl$_3$, 77.5 ppm, CD$_3$OD 49.3). Infrared spectra were recorded as a neat film on NaCl plates with a Perkin-Elmer Spectrum RX I FT-IR system. Microanalyses were performed by Atlantic Microlab, Inc. (Norcross, Ga.) and agree with ±0.4% of calculated values. All column chromatography was performed using the silica gel (Merck, 230-400 mesh, 60 Å) and CHCl$_3$/CH$_3$OH 10:1) as eluting solvent unless otherwise indicated. If not otherwise stated all spectroscopic data and yields refer to the free base.

S-(+)-2β-hydroxymethyl-3α-[bis(4-fluorophenyl)methoxy]tropane (2). A solution of 1a or 1b (3.03 mmol) in 8 mL of ether at 0° C. was added dropwise to a suspension of LiAlH$_4$ (115 mg, 3.03 mmol) in dry ethyl ether (8 mL). After the addition, the ice-H$_2$O bath was removed and the reaction mixture was allowed to warm to room temperature for 3 h. H$_2$O (0.3 mL) was added carefully at 0° C., followed by the addition of 0.5 mL of aqueous NaOH (2N). The resulting mixture was filtered, and the filtrate was dried (K$_2$CO$_3$). Ether was removed, and the residue was purified by flash column chromatography (eluting with 5-10% (CHCl$_3$/MeOH/NH$_4$OH; CMA) to give the product (1.02 g, 90%) as a colorless an oil. $[\alpha]^D{}_{25}$+37.5° (c=1.0, CHCl$_3$); $^1$H NMR (CDCl$_3$) δ 2.14-1.79 (m, 7H), 2.22 (s, 3H), 3.12 (m, 1H), 3.24 (m, 1H), 3.46 (dd, J=2.8, 10.4 Hz, 1H), 3.56 (d, J=6.0 Hz, 1H), 3.93 (dd, J=2.4, 10.0 Hz, 1H), 5.38 (s, 1H), 6.98 (m, 4H), 7.22 (m, 4H), ppm.

S-(+)-2β-Formyl-3α-[bis(4-fluorophenyl)methoxy]tropane (3). To a solution of oxalyl chloride (1.64 mL, 2.0 M solution in CH$_2$Cl$_2$, 3.28 mmol) under argon at −78° C. was added a solution of DMSO (469 mg, 6.02 mmol) in dry CH$_2$Cl$_2$ (1 mL). After 0.5 h, a solution of the alcohol 2 (1.02 g, 2.73 mmol) in dry CH$_2$Cl$_2$ (3 mL) was added and the reaction mixture was stirred for 1 h at −78° C., followed by addition of triethylamine (1.71 mL, 12.3 mmol) at the same temperature. The reaction mixture was then allowed to warm to room temperature and diluted with H$_2$O (20 mL). The organic layer was separated and the aqueous layer was extracted with CH$_2$Cl$_2$ (3×20 mL). The combined organic layers were dried (K$_2$CO$_3$) and concentrated to yield the aldehyde (994 mg, 98%). $^1$H NMR (CDCl$_3$) δ 2.21-1.58 (m, 7H), 2.23 (s, 3H), 3.06 (m, 1H), 3.57 (m, 1H), 3.99 (m, 1H), 5.37 (s, 1H) 6.98 (m, 4H), 7.24 (m, 4H), 9.59 (s, 1H), ppm. The aldehyde (3) was used in the following steps without further purification.

S-(+)-2β-Ethenyl-3α-[bis(4-fluorophenyl)methoxy]tropane (4). To a suspension of methyltriphenylphosphonium bromide (195 mg, 0.55 mmol) in dry tetrahydrofuran (THF) (3 mL) was added dropwise butyllithium (0.22 mL, 2.5 M solution in hexane, 0.55 mmol) at 0° C. under argon. The resulting yellow-orange solution was stirred for 30 min, and the ice-H$_2$O bath was then removed. The crude aldehyde (169 mg, 0.46 mmol) in 2 mL of THF was added, and the reaction mixture was stirred overnight at room temperature. The mixture was diluted with H$_2$O (20 mL), and the two layers were separated. The aqueous layer was extracted with CHCl$_3$ (3×20 mL). The combined organic layers were dried (K$_2$CO$_3$) and concentrated. The residue was purified by column chromatography to afford the product (105 mg, 62%) as an oil. IR: 1222 cm$^{-1}$; $^1$H NMR (CDCl$_3$) δ 2.08-1.75 (m. 6H), 2.21 (s, 3H), 2.47 (m, 1H), 2.99 (m, 1H), 3.07 (m, 1H), 3.32 (d, J=5.2 Hz, 1H), 4.88 (d, J=17.2 Hz, 1H), 4.96 (d, J=10.4 Hz, 1H), 5.37 (s, 1H), 5.96 (m, 1H), 6.98 (m, 4H), 7.30 (m, 4H), ppm; $^{13}$C NMR δ 24.9, 25.4, 36.1, 42.0, 50.1, 60.6, 65.9, 74.0, 79.8, 114.1, 115.1, 115.3, 128.3, 128.5, 138.5, 140.9, 160.8, 163.3, ppm.

S-(+)-2β-(2'-(methoxycarbonyl)eth-1'-enyl)-3α-[bis(4-fluorophenyl)methoxy]tropane (5). To a suspension of LiCl (80 mg, 1.89 mmol) in dry acetonitrile (8 mL) at room temperature under an argon atmosphere were added trimethyl phosphonoacetate (343 mg, 1.89 mmol), N,N-diisopropylethylamine (203 mg, 1.57 mmol), and the aldehyde (3, 583 mg, 1.57 mmol). The reaction mixture was allowed to stir for 24 h, acetonitrile was then removed under reduced pressure. The residue was diluted with H$_2$O (20 mL) and extracted with CHCl$_3$ (3×20 mL). The combined organic layers were dried (K$_2$CO$_3$) and concentrated. The crude product was purified by column chromatography (3% CMA) to afford the product (580 mg, 86%) as a light yellow solid. $^1$H NMR (CDCl$_3$) δ 2.16-1.78 (m, 6H), 2.20 (s, 3H), 2.58 (d, J=8.0 Hz, 1H), 3.12-3.00 (m, 2H), 3.34 (d, J=6.0 Hz, 1H), 3.70 (s, 3H), 5.35 (s, 1H), 5.68 (dd, J=1.2, 16 Hz, 1H), 7.08-6.97 (m, 5H), 7.24 (m, 4H), ppm; $^{13}$C NMR δ 25.4, 25.9, 36.4, 42.3, 49.4, 51.8, 60.9, 65.4, 73.6, 80.4, 115.5, 115.7, 120.8, 128.5, 128.6, 138.3, 151.0, 161.0, 163.4, 167.2, ppm; GC-MS (m/z) 427 (M+).

S-(+)-2β-(2'-(Methoxycarbonyl)ethyl)-3α-[bis(4-fluorophenyl)methoxy]tropane (6). A teaspoon of Raney Ni (in H$_2$O) was placed in a Parr bottle and washed (×3) with MeOH. The unsaturated compound 5 (580 mg, 1.36 mmol) in MeOH (40 mL) was added and the mixture was hydrogenated (40 psi) for 1.5 h. GC-MS showed the complete absence of starting material. The reaction mixture was then filtered and the solvents were evaporated under reduced pressure. The residue was purified by chromatography ($Et_2O/Et_3N=95/5$) to give (510 mg. 87.5%) as an oil. $^1$H NMR ($CDCl_3$) δ 2.06-1.48 (m, 9H), 2.17 (t, J=Hz, 2H), 2.21 (s, 3H), 2.94 (m, 1H), 3.03 (m, 1H), 3.16 (d, J=5.2 Hz, 1H), 3.66 (s, 3H), 5.34 (s, 1H), 6.99 (m, 4H), 7.25 (m, 4H), ppm; $^{13}$C NMR δ 24.8, 25.9, 28.3, 32.6, 35.9, 42.4, 45.6, 51.9, 61.3, 65.3, 73.1, 79.7, 115.4, 115.6, 128.5, 128.6, 138.6, 138.7, 160.9, 163.3, 174.1, ppm; GC-MS (m/z) 429 (M+).

S-(+)-2β-{[4-(4'-Nitrophenyl)butyryl]oxymethyl}-3α-[bis(4-fluorophenyl)methoxy]tropane (7). 4-(4'-Nitrophenyl)butyric acid (414 mg, 1.98 mmol) in $SOCl_2$ (8 mL) was refluxed for 3 h. Excess of $SOCl_2$ was removed, and the residue was dissolved in $CH_2Cl_2$ (20 mL). To the solution was added alcohol 2 (492 mg, 1.32 mmol), followed by the slow addition of triethylamine (1.1 mL, 7.9 mmol) at 0° C. The reaction mixture was then allowed to stir at room temperature for 3 h. The mixture was diluted with $H_2O$ (30 mL), and the two layers were separated, the aqueous layer was further extracted with $CH_2Cl_2$ (3×20 mL). The combined organic layers were dried ($K_2CO_3$) and concentrated. The residue was purified by column chromatography (eluting with $Et_2O/Et_3N=97/3$) to give the product (644 mg, 87%) as a brown oil. $[α]D_{25}$+3.5° (c=1.0, $CHCl_3$); $^1$H NMR ($CDCl_3$) δ 2.08-1.62 (m, 11H), 2.15 (s, 3H, N—$CH_3$), 2.72 (t, J=7.6 Hz, $COCH_2$), 3.07-2.98 (m, 2H), 3.30 (d, J=5.2 Hz, 1H), 4.00 (dd, J=9.2, 11.2 Hz, 1H, $CH_2O$), 4.09 (dd, J=6.0, 11.2 Hz, 1H, $CH_2O$), 5.34 (s, 1H, $OCHAr_2$), 6.96 (m, 4H, Ar—H), 7.24 (m, 4H, Ar—H), 7.32 (d, J=8.8 Hz, 2H, Ar—H), 8.15 (d, J=8.8 Hz, 2H, Ar—H), ppm; $^{13}$C NMR δ 24.2, 25.5, 25.9, 33.3, 34.9, 35.4, 45.8, 60.8, 62.8, 66.2, 70.1, 79.4, 115.1, 115.3, 123.7, 128.3, 128.4, 129.2, 138.4, 146.5, 149.2, 160.8, 163.2, 172.8, ppm; Anal. ($C_{32}H_{34}N_2F_2O_5$) for C, H, N.

S-(-)-2β-{[4-(4'-Aminophenyl)butyryl]oxymethyl}-3α-[bis(4-fluorophenyl)methoxy]tropane (8). A teaspoon of Raney Ni (in $H_2O$) was placed in a Parr bottle and washed (×3) with MeOH. To this were added the nitro compound MFZ 6-83 and MeOH/EtOAc (mL/mL). The mixture was hydrogenated at 30 psi overnight. Thin layer chromatography showed all the absence of starting material. The mixture was then filtered, and the filtrate was concentrated. The residue was purified by column chromatography (5% CMA) to give the product as an oil. $[α]^P_{25}$ −5.4° (c=1.0, $CHCl_3$); IR: 1727, 1603, 1221, cm$^{-1}$; $^1$H NMR ($CDCl_3$) δ 2.18-1.63 (m, 11H), 2.15 (s, 3H), 2.51 (t, J=7.6 Hz, 2H), 3.07-2.98 (m, 2H), 3.30 (d, J=5.2 Hz, 1H), 3.70-3.40 (brs, 2H, $NH_2$), 3.95 (dd, J=9.2, 11.0 Hz, 1H), 4.10 (dd, J=6.0, 11.0 Hz, 1H), 5.32 (s, 1H), 6.63 (d, J=8.8 Hz, 2H), 6.96 (m, 6H), 7.22 (m, 4H), ppm; $^{13}$C NMR δ 24.6, 25.7, 27.0, 33.8, 34.5, 35.9, 42.1, 45.8, 61.1, 63.0, 66.2, 70.4, 79.6, 115.3, 115.5, 128.6, 128.7, 129.5, 131.6, 138.6, 144.7, 161.0, 163.4, 173.7, ppm.

S-(-)-2β-{[4-(3'-iodo-4'-Aminophenyl)butyryl]oxymethyl}-3α-[bis(4-fluorophenyl)methoxy]tropane. Compound 8 (115 mg, 0.22 mmol) was dissolved in acetic acid (4 mL). To the solution was added extremely slowly ICl (42 mg, 0.26 mmol) in acetic acid (2 mL) over 3 h. After the addition, the solvent was removed under reduced pressure. The residue was then diluted with $H_2O$ (10 mL), basified with $NaHCO_3$, and extracted with $CHCl_3$ (3×10 mL). The combined organic layers were dried ($K_2CO_3$) and concentrated. The residue was purified by column chromatography (eluent: $Et_2O/Et_3N=97:3$) to afford the product (45 mg, 32%) as an oil. $[α]^P_{25}$ −5.4° (c=1.0, $CHCl_3$); IR: 1728, 1603, 1221, cm$^{-1}$; $^1$H NMR ($CDCl_3$) δ 2.18-1.70 (m, 11H), 2.16 (s, 3H), 2.47 (t, J=7.6 Hz, 2H), 3.09-2.98 (m, 2H), 3.31 (d, J=4.8 Hz, 1H), 4.02-3.90 (m, 3H), 4.09 (dd, J=6.0, 11.2 Hz, 1H), 5.33 (s, 1H), 6.68 (d, J=7.6 Hz, 1H), 6.97 (m. 5H), 7.23 (m, 4H), 7.46 (s, 1H), ppm; $^{13}$C NMR δ 24.6, 25.7, 26.8, 33.6, 33.9, 35.9, 42.1, 45.8, 61.1, 63.0, 66.3, 70.4, 79.6, 84.5, 114.9, 115.3, 115.5, 128.6, 128.7, 129.7, 133.3, 138.6, 138.8, 145.1, 161.0, 163.5, 173.5, ppm.

S-(+)-N-nor-2β-Carboethoxy-3α-[bis(4-fluorophenyl)methoxy]tropane (9). Compound 1b (652 mg, 1.57 mmol) was dissolved in 1,2-dichloroethane. To the solution was added 1-chloroethyl chloroformate (ACE-Cl, 0.68 mL, 6.28 mmol) and $Na_2CO_3$ (833 mg, 7.85 mmol), and the mixture was warmed to reflux for 3 h. Thin layer chromatography (TLC) showed the starting material disappeared. After cooling to room temperature, the reaction mixture was filtered. Solvent in the filtrate was removed. The residue was then dissolved in MeOH (20 mL), and the solution was then refluxed for 1 h. Methanol was removed in vacuo. The residue was diluted with $H_2O$ (50 mL), basified with $NaHCO_3$, and extracted with $CHCl_3$ (3×50 mL). The combined organic layer was dried ($K_2CO_3$) and concentrated. The residue was purified by column chromatography (eluting with 5% CMA) to give the product (610 mg, 97%) as an oil. $[α]^P_{25}$+33.8° (c=1.0, $CHCl_3$); IR: 3326, 1728, 1212, cm$^{-1}$; $^1$H NMR ($CDCl_3$) δ 1.23 (t, J=7.2 Hz, 3H), 1.97-1.65 (m, 5H), 2.22-2.06 (m, 2H), 2.65 (s, 1H), 3.48 (m, 1H0, 3.79 (m, 1H), 3.83 (d, (J=Hz, 1H), 4.17-4.04 (m, 2H), 5.37 (s, 1H), 7.00 (dd, J=Hz, 4H), 7.25 (m, 4H), ppm; $^{13}$C NMR δ 14.6, 28.9, 29.2, 36.0, 50.6, 53.5, 55.8, 51, 71.2, 80.6, 115.4, 115.6, 128.5, 128.7, 138.3, 161.0, 163.4, 173.2, ppm; GC-MS (m/Z) 401 (M+).

S-(+)-N-Allyl-2β-carboethoxy-3α-[bis(4-fluorophenyl)methoxy]tropane (11). Compound 9 (85 mg, 0.21 mmol) and allyl bromide (51 mg, 0.42 mmol) were combined in dimethylformamide (DMF) (3 mL). To the solution was added $K_2CO_3$ (58 mg, 0.42 mmol), and the mixture was heated to 65° C. overnight. $H_2O$ (20 mL) was added, and the mixture was extracted with $CHCl_3$ (3×30 mL). The combined organic layer was dried ($K_2CO_3$) and concentrated. The residue was purified by column chromatography (eluting with 3% CMA) to give the product (86 mg, 92%) as an oil. $^1$H NMR ($CDCl_3$) δ 1.23 (t, J=7.2 Hz, 3H), 2.18-1.58 (m, 6H), 2.69 (m, 1H), 2.81 (dd, J=7.2, 13.6 Hz, 1H), 2.94 (dd, J=5.6, 13.6 Hz, 1H), 3.15 (m, 1H), 3.68 (m, 1H), 4.00 (d, J=2.0 Hz, 1H), 4.18-4.02 (m, 2H), 5.12-5.02 (m, 2H), 5.34 (s, 1H), 5.78 (m, 1H), 6.98 (m, 4H), 7.25 (m, 4H), ppm; $^{13}$C NMR δ 14.2, 24.6, 25.9, 36.3, 51.8, 56.7, 59.8, 60.2, 60.4, 70.7, 80.3, 115.2, 115.4116.3, 128.3, 128.4, 136.8, 138.3, 138.4, 160.8, 163.3, 172.5, ppm.

S-(+)-N-Butyl-2β-carboethoxy-3α-[bis(4-fluorophenyl)methoxy]tropane (10). Compound 10 was obtained in 87% yield by the procedure described above for compound II using butyl bromide. $[α]^P_{25}$+20.4° (c=1.0, $CHCl_3$); IR: 1729, 1603, 1223, cm$^{-1}$; $^1$H NMR ($CDCl_3$) δ 0.86 (t, J=7.2 Hz, 3H), 1.24 (t, J=7.2 Hz, 3H), 1.40-1.20 (m. 4H), 2.21-1.74 (m, 8H), 2.68 (m, 1H), 3.12 (m, 1H), 3.69 (m, 1H), 3.99 (d, J=4.8 Hz, 1H), 4.09 (m, 2H), 5.34 (s, 1H), 6.98 (m, 4H), 7.23 (m, 4H), ppm; $^{13}$C NMR δ 14.3, 14.4, 20.7, 24.9, 26.2, 31.5, 36.5, 52.1, 53.5, 60.6, 60.7, 61.0, 71.1, 80.5, 110.0, 115.4, 115.6, 128.5, 128.6, 138.8, 161.0, 163.5, 172.7, ppm.

S-(+)-2β-Carbomethoxy-3α(-[bis(4-chlorophenyl)methoxy]tropane (14). S-(+)-alloecgonine methyl ester (Zou et al., *J. Med. Chem.*, 46, 2908-2916 (2003)) (309 mg, 1.55 mmol), 4,4'-dichlorobenzhydrol (786 mg, 3.10 mmol), p-toluenesulfonic acid monohydrate (443 mg, 2.33 mmol), and benzene (15 mL) were placed in a 50 mL round-bottom flask fitted with a Dean-Stark trap and condenser. The reaction mixture was heated to reflux for 24 h. The solvent was then removed, and the residue was diluted with water (20 mL), basified with $NH_4OH$ to pH 9, and extracted with $CHCl_3$ (3×20 mL). The combined organic layer was dried ($K_2CO_3$) and concentrated. The residue was purified by column chromatography ($CHCl_3$/MeOH/$NH_4OH$, 97:3:1) to afford S-(+)-14 (472 mg, 70%) as an oil, which solidified slowly to a white solid after standing at room temperature. Mp: 109-110° C. (lit. mp (Meltzer et al., *J. Med. Chem.*, 39, 371-379 (1996)): 110-112° C.). $[\alpha]D25$ +17.3° (c=1.0, $CHCl_3$); IR: 1732, 1069, $cm^{-1}$; $^1$H NMR ($CDCl_3$) δ 2.17-1.68 (m, 6H), 2.18 (s, 3H), 2.71 (m, 1H), 3.09 (m, 1H), 3.59 (m, 1H), 3.68 (s, 3H), 3.95 (d, J=4.8 Hz, 1H), 5.32 (s, 1H), 7.30-7.12 (m, 8H), ppm; GC-MS (m/z) 433 (M+); Anal. ($C_{23}H_{25}NCl_2O_3$) for C,H,N.

(±)-14 was prepared by the same procedure in 75% yield. Mp: 108-110° C. The IR, $^1$H NMR, and GC-MS spectra for (±)-14 were identical to S-(+)-14. Anal. ($C_{23}H_{25}NCl_2O_3$) for C,H,N.

S-(+)-2β-Carboethoxy-3α-[bis(4-chlorophenyl)methoxy]tropane (15). S-(+)-15 was prepared in 78% yield according to the above procedure. Mp: 88-89.5° C. $[\alpha]D24$ +17.00 (c=1.0, $CHCl_3$); IR: 1733, 1222, $cm^{-1}$; 1H NMR ($CDCl_3$) δ 1.22 (t, J=7.0 Hz, 3H), 2.16-1.65 (m, 6H), 2.18 (s, 3H), 2.68 (m, 1H), 3.08 (m, 1H), 3.58 (m, 1H), 3.97 (d, J=4.8 Hz, 1H), 4.22-4.00 (m, 2H), 5.30 (s, 1H), 7.30-7.16 (m, 8H), ppm; GC-MS (m/z) 447 (M+); anal. ($C_{24}H_{27}NCl_2O_3$) for C,H,N.

(±)-15 was prepared in 74% yield by the same procedure. Mp: 87.5-89.5° C. The IR, $^1$H NMR, and GC-MS spectra for (±)-15 were identical to S-(+)-15. Anal. ($C_{24}H_{27}NCl_2O_3$) for C,H,N.

Dopamine Transporter Binding Assay. Male Sprague-Dawley rats (200-250 g, Taconic, Germantown, N.Y.) were decapitated and their brains removed to an ice-cooled dish for dissection of the caudate putamen. The tissue was homogenized in 30 volumes of ice-cold modified sucrose using a Brinkman polytron and centrifuged at 20,000×g for 10 min at 4° C. The resulting pellet was then washed two more times by re-suspension in ice-cold buffer and centrifugation at 20,000×g for 10 min at 4° C. Fresh homogenates were used in all experiments.

Binding assays were conducted in modified sucrose buffer on ice. The total volume in each tube was 0.5 mL and the final concentration of membrane after all additions was 0.5% (w/v) corresponding to 200-300 mg of protein/sample. Triplicate samples of membrane suspension were preincubated for 5 min in the presence or absence of the compound being tested. [$^3$H]WIN 35,428 (2-β-carbomethoxy-3-β-(4-fluorophenyl)tropane 1,5-naphthalene disulfonate; specific activity 82.4 Ci/mmol, from New England Nuclear, Boston, Mass., final concentration 1.5 nM) was added and the incubation was continued for 1 hr on ice. The incubation was terminated by the addition of 3 mL of ice-cold buffer and rapid filtration through Whatman GF/B glass fiber filter paper (presoaked in 0.1% bovine serum albumin (BSA) in water to reduce nonspecific binding) using a Brandel Cell Harvester (Gaithersburg, Md.). The filters were washed with three additional 3 mL washes and transferred to scintillation vials. Absolute ethanol (0.5 mL) and Beckman Ready Value Scintillation Cocktail (2.75 mL) were added to the vials which were counted the next day at an efficiency of about 36%. Under these assay conditions, an average experiment yielded approximately 6,000 dpm total binding per sample, and approximately 250 dpm non-specific binding, defined as binding in the presence of 100 μM cocaine. Each compound was tested with concentrations ranging from 0.01 nM to 100 μM for competition against binding of [$^3$H]WIN 35,428, in three independent experiments, each performed in triplicate.

Saturation and displacement data were analyzed by the use of the nonlinear least squares curve-fitting computer program PRISM. Data from replicate experiments were modeled together to produce a set of parameter estimates and the associated standard errors of these estimates. In each case, the model reported fit significantly better than all others according to the F test at p<0.05. The $K_i$ values reported are the dissociation constants derived for the unlabeled ligands.

[$^3$H]Nisoxetine Binding Assay. Membranes from frozen frontal cortex dissected from male Sprague-Dawley rats (Taconic Labs, Germantown, N.Y.) were homogenized in 20 volumes (w/v) of 50 mM Tris containing 120 mM NaCl and 5 mM KCl (pH 7.4 at 25° C.), using a Brinkman Polytron (at setting 6 for 20 sec). The tissue was centrifuged at 50,000×g for 10 min at 4° C. The resulting pellet was resuspended in buffer and recentrifuged. The final pellet was resuspended in cold buffer to a concentration of 80 mg/mL (original wet weight). Ligand binding experiments were conducted in assay tubes containing 0.5 mL buffer, 0.5 μM [$^3$H]nisoxetine (New England Nuclear, Boston Mass.), and 8 mg frontal cortex tissue. The reaction was started with the addition of the tissue and the tubes were incubated for 60 min at 0-4° C. The incubation was terminated by rapid filtration through Whatman GF/B filters, presoaked in 0.05% polyethylenimine, using a Brandel Cell Harvester (Brandel Instruments Gaithersburg, Md.). The filters were washed twice with 5 mL cold buffer, transferred to scintillation vials to which Beckman Ready Safe was added. Nonspecific binding was determined using 1 μM desipramine. Data were analyzed using GraphPad Prism software (San Diego, Calif.).

[$^3$H] Citalopram Binding Assay. Membranes from frozen rat midbrain were homogenized in 20 volumes (w/v) of 50 mM Tris containing 120 mM NaCl and 5 mM KCl (pH 7.4 at 25° C.), using a Brinkman Polytron (at setting 6 for 20 see). The tissue was centrifuged at 20,000×g for 10 min at 4° C. The resulting pellet was resuspended in buffer and recentrifuged. The final pellet was resuspended in cold buffer to a concentration of 15 mg/mL (original wet weight). Ligand binding experiments were conducted in assay tubes containing 0.5 mL of buffer, 1.4 nM [$^3$H]citalopram (New England Nuclear, Boston, Mass.), and 1.5 mg midbrain tissue. The reaction was started with the addition of the tissue and the tubes were incubated for 60 min at 25° C. (room temperature). The incubation was terminated by rapid filtration through Whatman GF/B filters (presoaked in 0.3% polyethylenimine in water) using a Brandel Cell Harvester (Brandel Instruments Gaithersburg, Md.). The filters were washed twice with 5 mL cold buffer, transferred to scintillation vials to which Beckman Ready Safe was added. Nonspecific binding was determined using 10 μM fluoxetine (RBI, Natick, Mass.). Data were analyzed using GraphPad Prism software (San Diego, Calif.).

[$^3$H]Pirenzepine Binding Assay. Membranes from frozen rat brains excluding cerebellum were thawed in ice-cold buffer (10 mM Tris-HCl, 320 mM sucrose, pH 7.4) and homogenized with a Brinkman polytron in a volume of 10 mL/gm of tissue. The homogenate was centrifuged at 1,000×g for 10 min at 4° C. The resulting supernatant was then centrifuged at 10,000×g for 20 min at 4° C. The resulting pellet was resuspended in a volume of 200 mg/mL in 10 mM Tris buffer (pH 7.4). Ligand binding assays were conducted in tubes containing 0.5 mL of buffer (10 mM Tris-HCl, 5 mM $MgCl_2$), 3 nM [$^3$H]pirenzepine (New England Nuclear, Boston, Mass.), and 20 mg of brain tissue. The reaction was started with the addition of the tissue and the tubes were incubated for 60 min in a 37° C. water bath. The incubation was terminated by the addition of 5 mL of ice-cold buffer (10 mM Tris-HCl, pH 7.4) and rapid filtration through Whatman GF/B glass fiber filter paper (presoaked in 0.5% polyethylenimine) using a Brandel Cell Harvester (Brandel Instruments, Gaithersburg, Md.). The filters were washed twice with 5 mL cold buffer, and transferred to scintillation vials to which absolute ethanol and Beckman Ready Safe was added. Quinuclidinyl benzilate (QNB), 100 μM final concentration, was used to determine non-specific binding. Data were analyzed by using GraphPad Prism software (San Diego, Calif.).

Dopamine Uptake Assay. The tissue was homogenized in ice cold buffer (5 mM HEPES, 0.32M sucrose) using 10 strokes with a Teflon glass homogenizer followed by centrifugation at 1000 g for 10 min at 4° C. The supernatant was saved and recentrifuged at 10,000 g for 20 min at 4° C. The supernatant was then discarded and the pellet was gently resuspended in an ice cold incubation buffer (127 mM NaCl, 5 mM KCl, 1.3 mM $NaH_2PO_4$, 1.2 mM $MgSO_4$, 2.5 mM $CaCl_2$, 1.498 mM HEPES acid, 10 mM D-Glucose, 1.14 mM L-ascorbic acid, pH 7.4) and placed on ice for 15 min. The synaptosomal tissue preparation was incubated in buffer in glass test tubes at 37° C. to which 10 μM pargyline and either the drug being tested or no drug was added, as appropriate. After a 10 minute pre-incubation in the presence of drug, [$^3$H] dopamine (final concentration, 0.5 nM) (Amersham Biosciences, Piscataway, N.J.) was added to each tube and the incubation was carried on for 5 min. The reaction was terminated by the addition of 3 mL ice cold buffer to each tube and rapid filtration through Whatman GF/B glass fiber filter paper (presoaked in 0.1% polyethylenimine in water) using a Brandel cell harvester (Brandel Instruments, Gaithersburg, Md.). After filtration, the filters were washed with two additional 5 mL washes and transferred into scintillation vials. Beckman Ready Value (Beckman-Coulter Instruments, Fullerton, Calif.) was added and the vials were counted the next day using a Beckman 6000 liquid scintillation counter (Beckman Coulter Instruments, Fullerton, Calif.). The reported values represent specific uptake from which nonspecific uptake was subtracted (defined as uptake in the presence of 100 μM (−)cocaine HCl). Data were analyzed using the nonlinear regression analysis of GraphPad Prism Software, (San Diego Calif.).

Cocaine Discrimination Assay. Rats weighing 320-350 g served as subjects. They were fed daily about 15 g of standard lab chow at least 30 min after testing. Subjects were tested daily in two-lever operant-conditioning chambers (Med Associates, Model ENV 007, St. Albans, Vt., USA) that were housed within light- and sound-attenuating enclosures. White noise was present throughout testing to mask extraneous sounds. Ambient illumination was by a lamp in the top center of the front panel (houselight). Levers were set 17 cm apart, with pairs of lamps (light-emitting diodes, LEDs) above each of the levers, also on the front panel. A downward force on either lever of 0.4 N through about 1 mm was defined as a response, and produced an audible click. Reinforced responses dispensed one 45-mg pellet (BioServe, Frenchtown N.J., USA) into a food tray centered between the levers on the front panel of the chamber. On-line experimental control and data collection were by computers with Med Associates interfacing equipment and operating software (Med Associates, St. Albans, Vt.).

Subjects were initially trained to press both levers under a 20-response fixed-ratio (FR 20) schedule of food reinforcement and to discriminate IP injections of 29 μmol/kg cocaine (10 mg/kg) from IP injections of saline. After cocaine injection, responses on only one lever were reinforced; after saline injection, responses on the other lever were reinforced. The assignment of cocaine- and saline-appropriate levers was counterbalanced across rats. Immediately after injection, rats were placed inside the experimental chambers. A 5-min time-out period, during which the houselight and LEDs were extinguished and responding had no scheduled consequences preceded the illumination of the houselight and the LEDs. Only responses on the appropriate lever were reinforced, and responses on the inappropriate lever reset the FR response requirement. Each food presentation was followed by a 20-sec time-out period during which all lights were off, and responding had no scheduled consequences. Experimental sessions ended after 20 food presentations or 15 min, whichever occurred first. Training sessions with cocaine (C) and saline (S) injections were conducted daily 5 days per week, and ordered in a double alternation sequence [e.g., . . . SCCS . . . ].

Testing was initiated when performances reached criteria of at least 85% appropriate responding overall and during the first FR 20 of the session over four consecutive sessions. Tests were conducted with different doses of cocaine or doses of the novel compounds. After a test session, a subject was required to meet the above performance criteria over two consecutive (cocaine and saline) training sessions in order to be tested again. Repeated test sessions were conducted, with at least two training sessions between tests, until entire dose-effects were determined in each subject. Test sessions were identical to training sessions, with the exception that 20 consecutive responses on either lever were reinforced.

For each of the rats studied in the cocaine-discrimination procedure, the overall response rate and the percentage of responses occurring on the cocaine-appropriate lever were calculated. The mean values were calculated for each measure at each drug dose tested (FIG. 1A-F). If less than half of the rats responded at a particular dose, no mean value was calculated for percentage of cocaine-appropriate responding at that dose. At least 20% cocaine-appropriate responding was adopted as a conservative criterion at which to assume a significant difference from saline; 80% or higher cocaine-appropriate responding was taken as similar to the training dose of cocaine, and intermediate levels of cocaine-appropriate responding were considered partial substitution. The 2-substituted BZT analogues with 4',4"-diF-substitutions fully substituted for cocaine, whereas the parent compound lacking a 2 substituent ("AHN 1-055," in which $R^4$ is hydrogen), and the 2-substituted BZT analogues with 4',4"-diCl-substitutions did not fully substitute for cocaine.

Figure 2B:
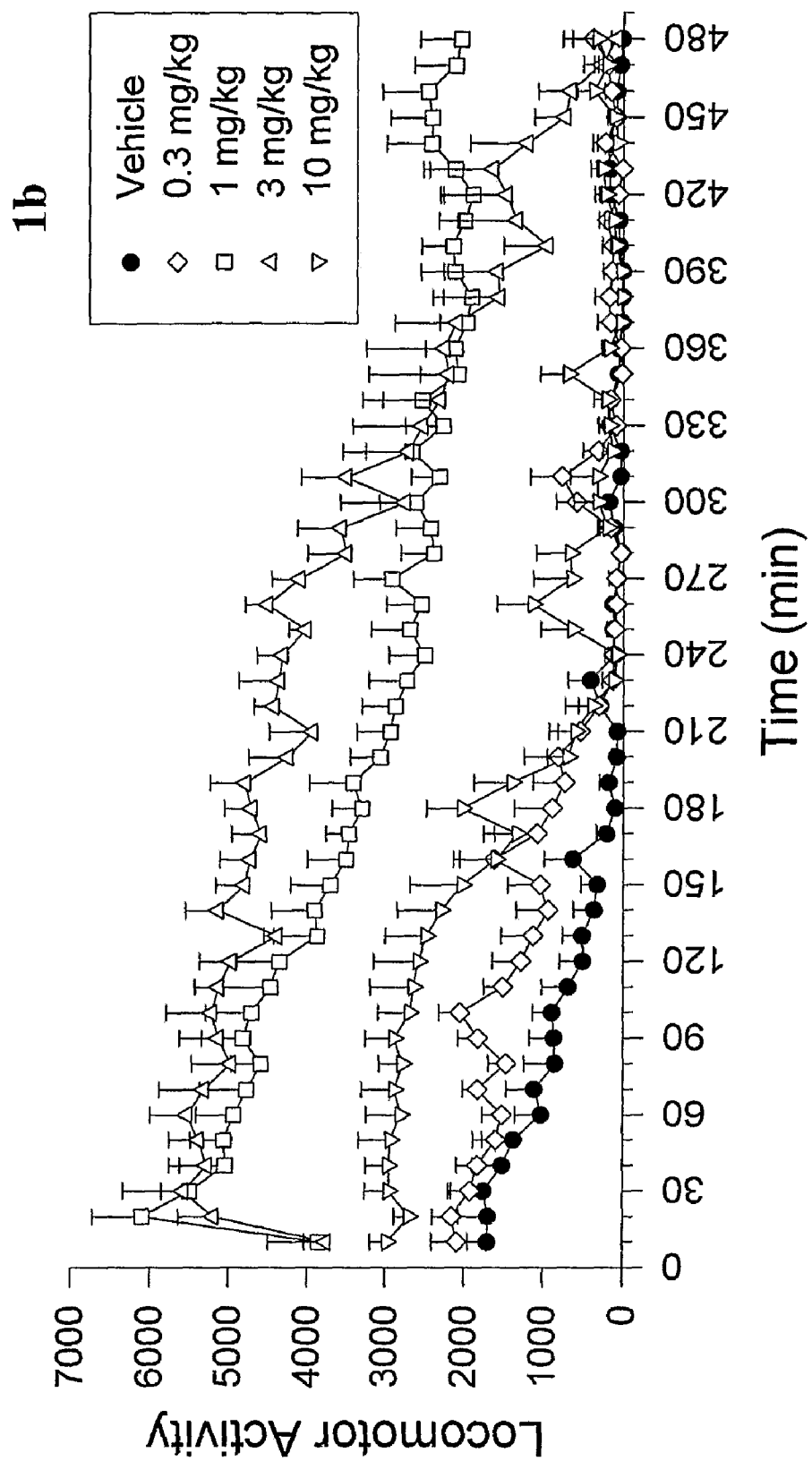
FIG. 2B represents injection of 1b.
Figure 2C:
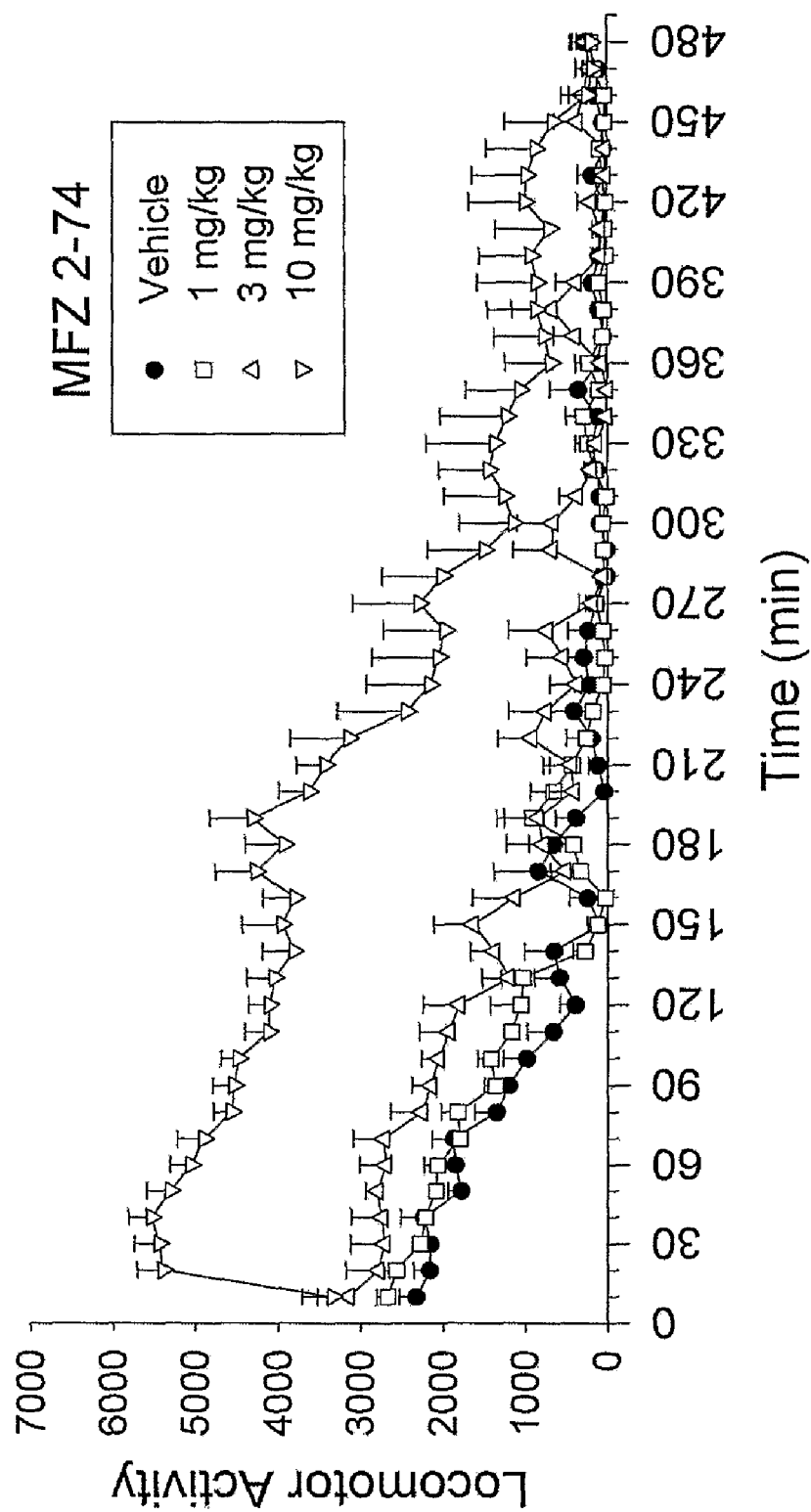
FIG. 2C represents injection of MFZ 2-74 ($R^1$=Me; $R^{2,3}$=F; $R^4$=$CO_2$-$^i$Pr).
Figure 2D:
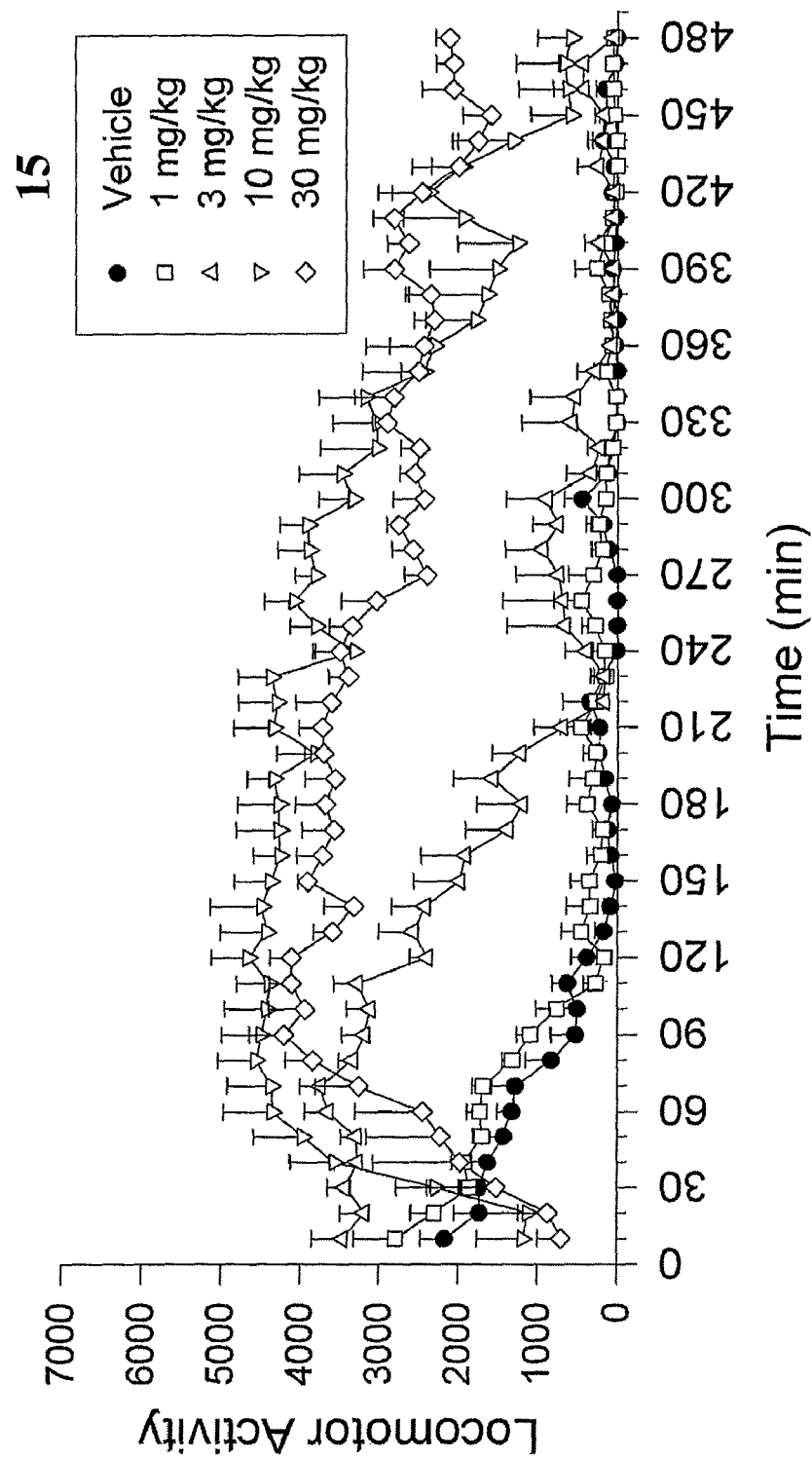
FIG. 2D represents injection of 15.
Figure 2E:
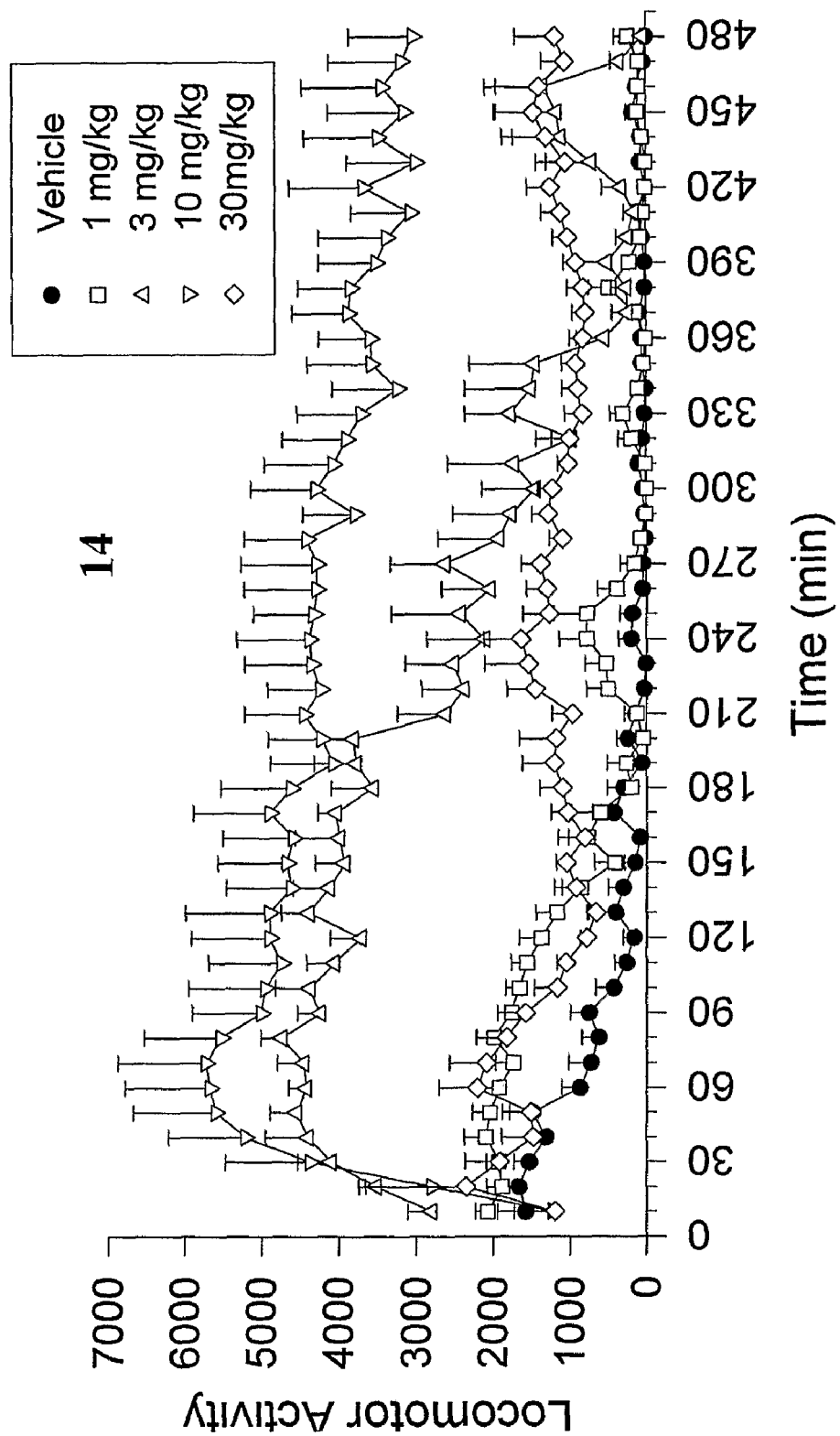
FIG. 2E represents injection of 14.

Locomotor Activity. For the assessment of horizontal locomotor activity (ambulation), mice were tested alone in clear acrylic experimental chambers (40 $cm^3$). Around the outside of two perpendicular adjoining walls of the chambers were arrays of light sensitive detectors, spaced 2.5 cm apart. Infrared light sources were mounted outside the opposing walls and directed at the detectors (Omnitech Electronics, Columbus, Ohio, USA). Each interruption of a single light beam registered by the detectors resulted in the tabulation of one horizontal activity count. Mice were injected and immediately placed in the apparatus for 8 h. Total activity count data were collected each 10 min and all data were analyzed using two-way analysis of variance (ANOVA) and post-hoc Tukey's Test to determine significance of effects of individual doses at different time periods (FIG. 2A-E). The duration of effects was greater than that typically obtained with cocaine, and that the maximal stimulation produced was generally (i) from 30 to 60 min after injection of compound 1a (FIG. 2A); (ii) from 20 to 120 min after injection of compound 1b (FIG. 2B); (iii) from 20 to 60 min after injection of compound MFZ 2-74 ($R^1$=Me; $R^{2,3}$=F; $R^4$=$CO_2$-$^i$Pr) (FIG. 2C); (iv) from 90 to 240 min after injection of compound 15 (FIG. 2D); and (v) from 50 to 90 min after injection of compound 14 (FIG. 2E).

In vivo binding of [$^{125}$I]RTI-121. Each animal received an i.v. injection of 2 μCi of [$^{125}$I]RTI-121. Two hours after administration of [$^{125}$I]RTI-121, the animals were sacrificed by cervical dislocation. In each mouse, displacement of [$^{125}$I]RTI-121 was examined by giving an i.p. injection of one of the displacers at various doses and times relative to sacrifice, Displacement by test drugs at various doses was examined at various times after their injection, with each data point determined in sets of approximately six mice. Whole brains were rapidly removed and striatum and cerebellum were dissected on ice. Following dissection, each brain region was placed into separate plastic vials (Rohren Tubes, 55×12 mm), weighed and tissue radioactivity was measured using an automated gamma counter (ICN Biomedicals, INC, Micromedic Systems, 10/600 PLUS).

Figure 3A:
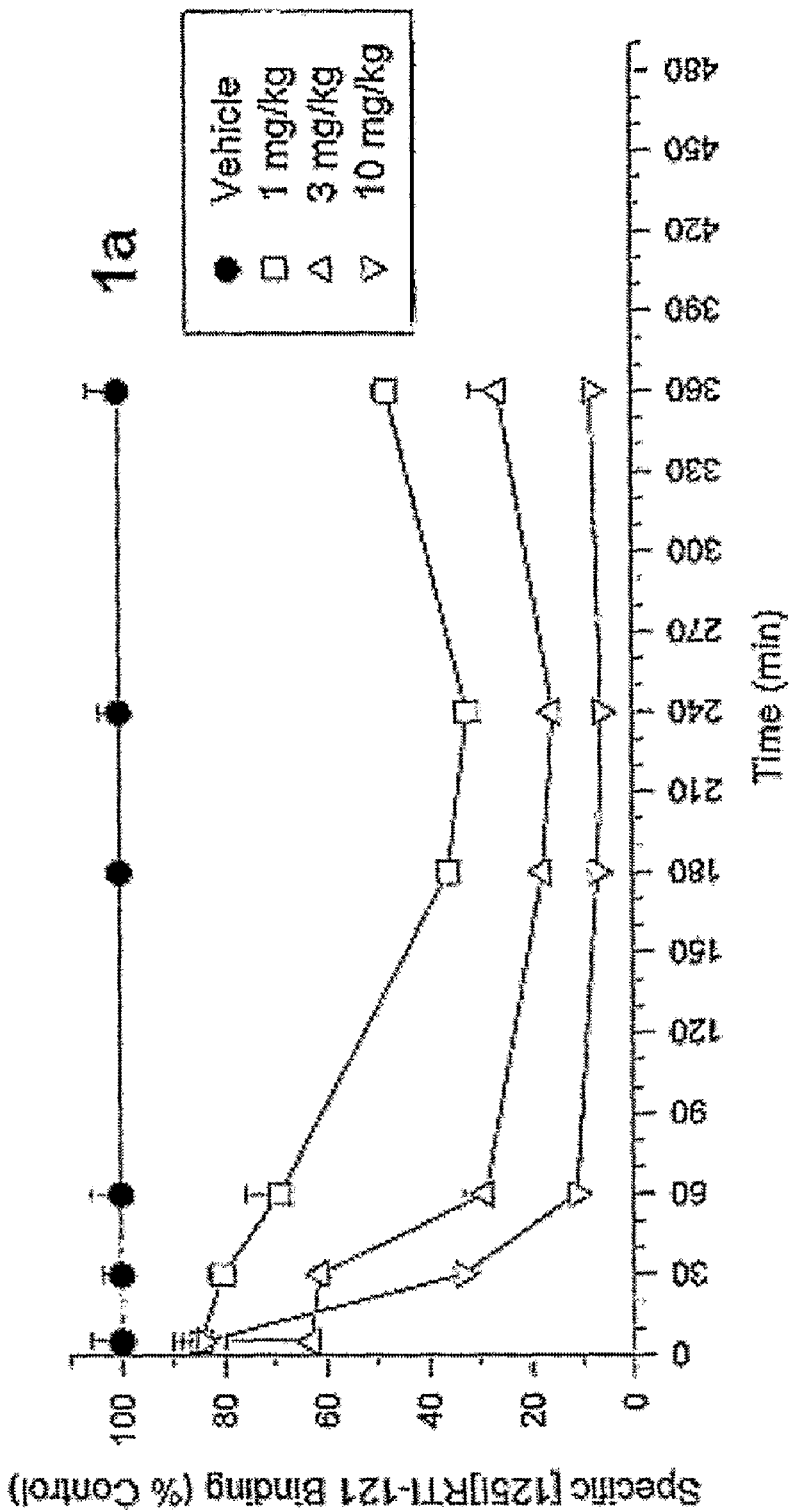
Figure 3B:
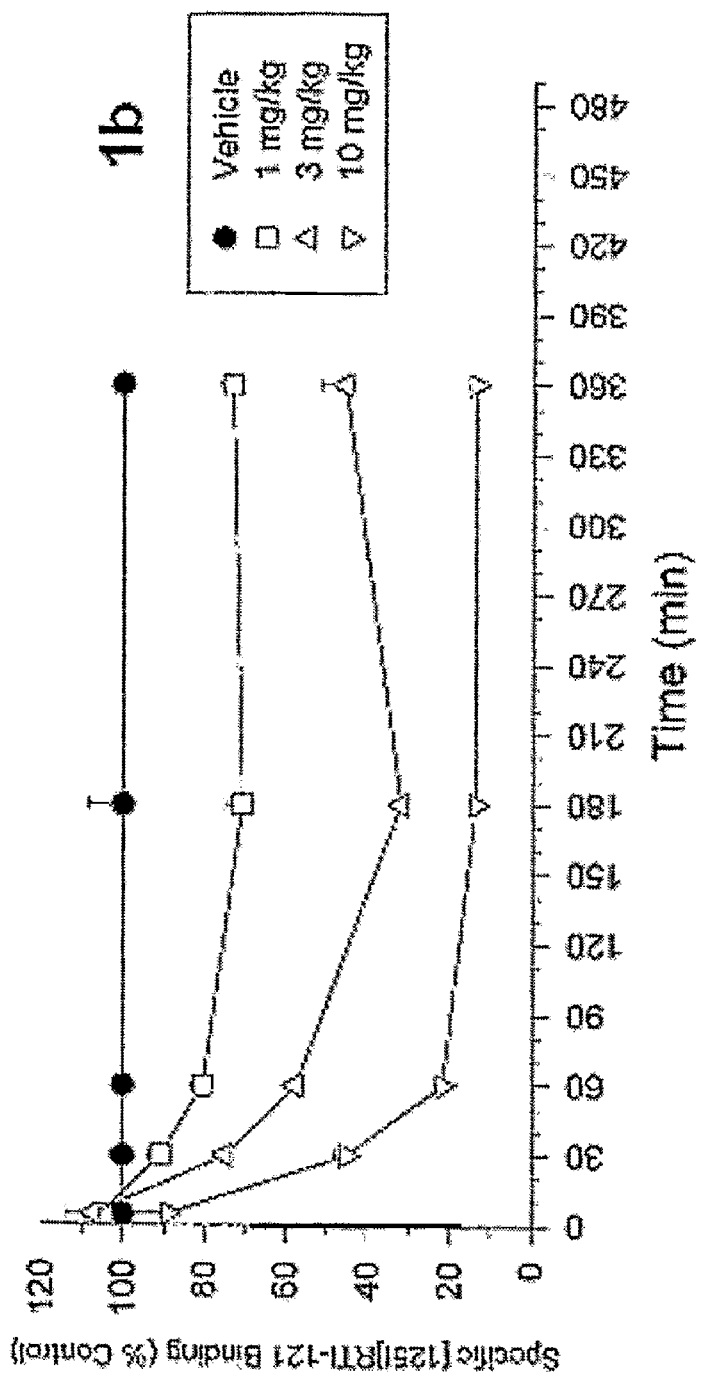
FIG. 3B represents injection of 1b.
Figure 3C:
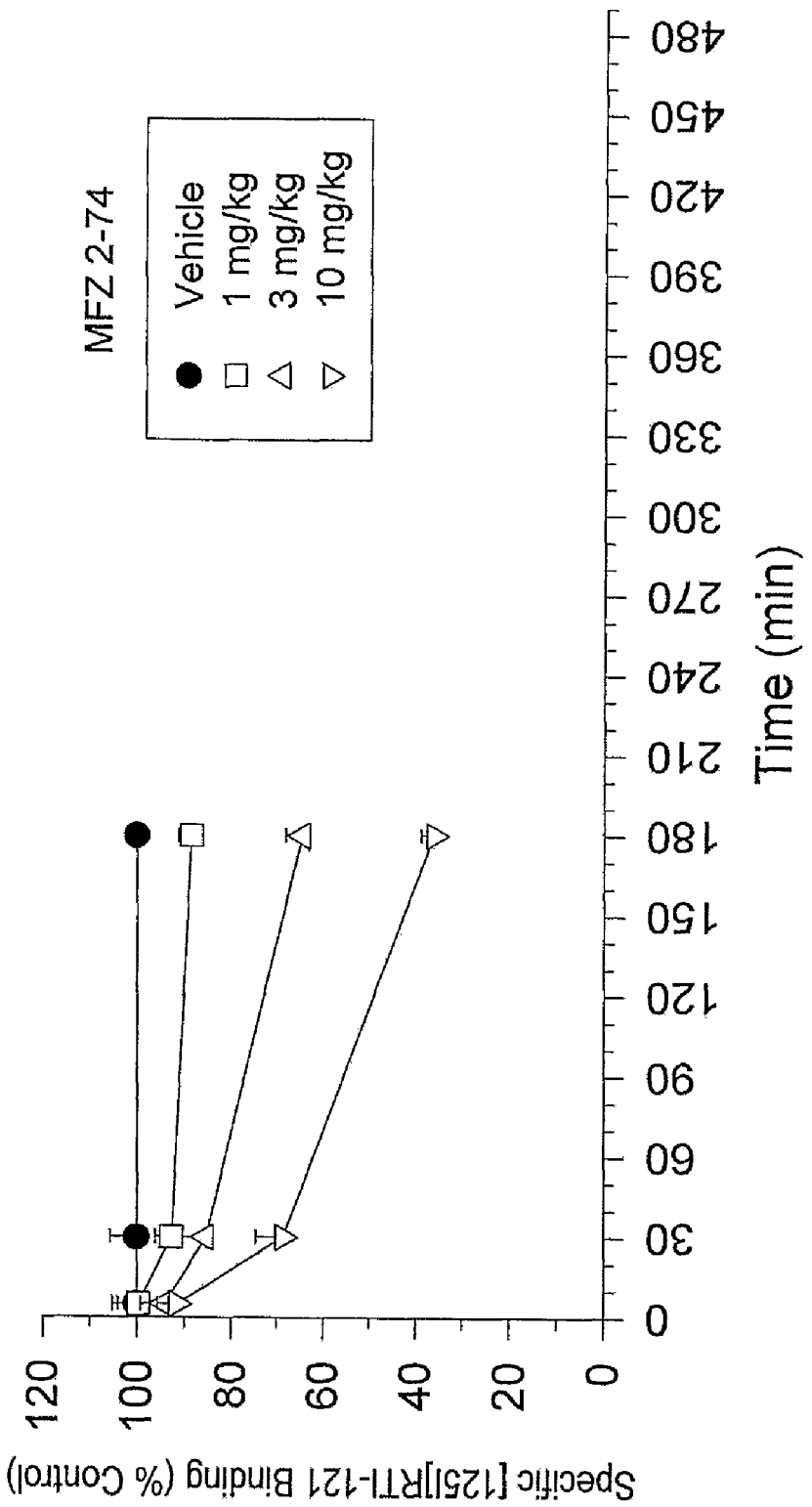
FIG. 3C represents injection of MFZ 2-74 ($R^1$=Me; $R^{2,3}$=F; $R^4$=$CO_2$-$^i$Pr).
Figure 3D:
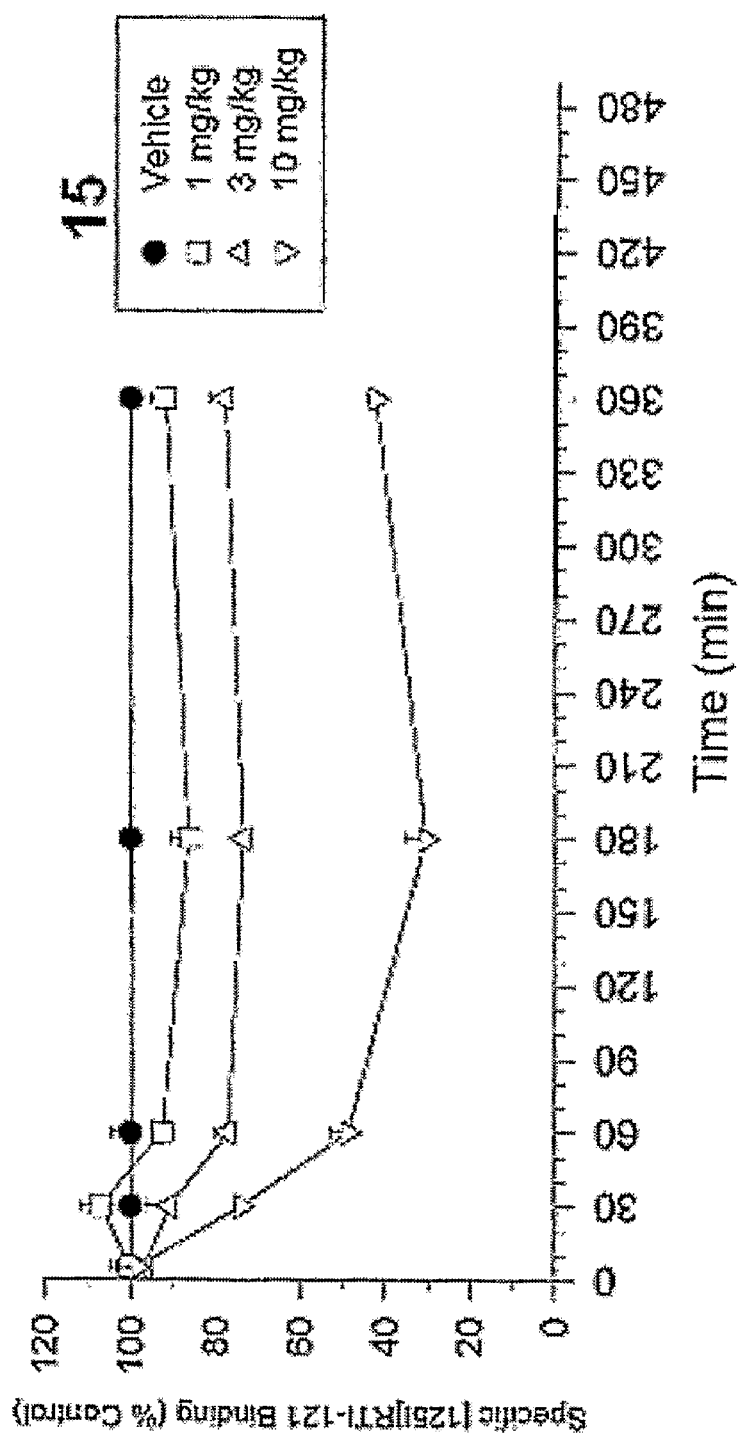
FIG. 3D represents injection of 15.
Figure 3E:
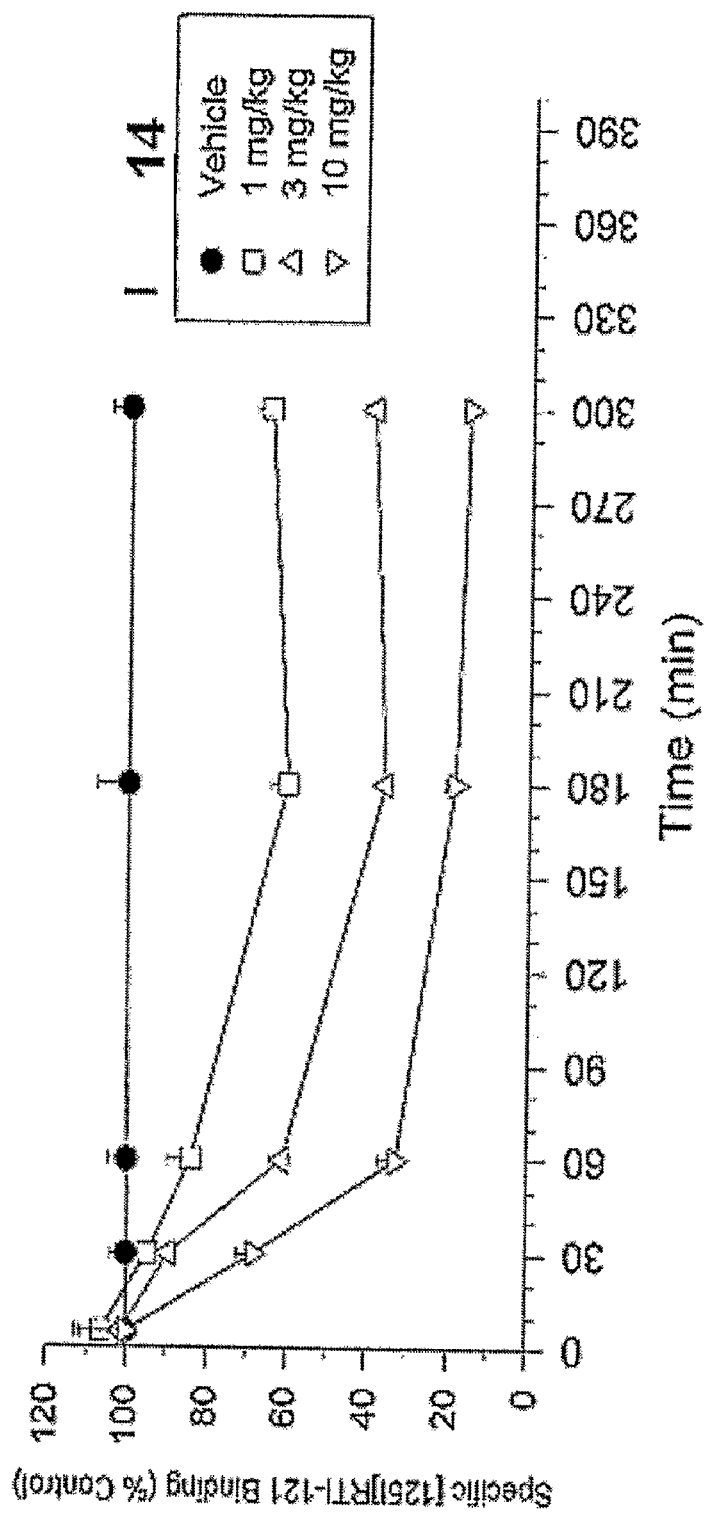
FIG. 3E represents injection of 14.

Regional radioactivity levels were divided by weight (gram) of the tissue (CPM/tissue weight). Specific binding was calculated as CPM/tissue weight in striatum divided by cerebellum minus 1 (S/C−1), which is based on the observation that dopaminergic transporter sites are highly concentrated in the striatum and relatively absent in the cerebellum. These values were expressed as a percentage of specific binding after vehicle injection. Data were analyzed using two-way analysis of variance (ANOVA), and a post-hoc Tukey's test was used to determine significance of effects for individual doses at different time periods following IP injection of compound 1a (FIG. 3A), 1b (FIG. 3B), MFZ 2-74 ($R^1$=Me; $R^{2,3}$=F; $R^4$=CO$_2$-$^i$Pr) (FIG. 3C), 15 (FIG. 3D), and 14 (FIG. 3E). Maximal displacement of [$^{125}$I]RTI-121 was (i) obtained between 60 and 360 min after injection of compound 1a (FIG. 3A); (ii) obtained at some point beyond 180 min after injection of compound 1b (FIG. 3B); (iii) not obtained and would likely be obtained at some point beyond 3 hours after injection of compound MFZ 2-74 (FIG. 3C); (iv) obtained between 180 and 360 min after injection of compound 15 (FIG. 3D); and (v) obtained at some point beyond 180 min after injection of compound 14 (FIG. 3E).

Figure 4A:
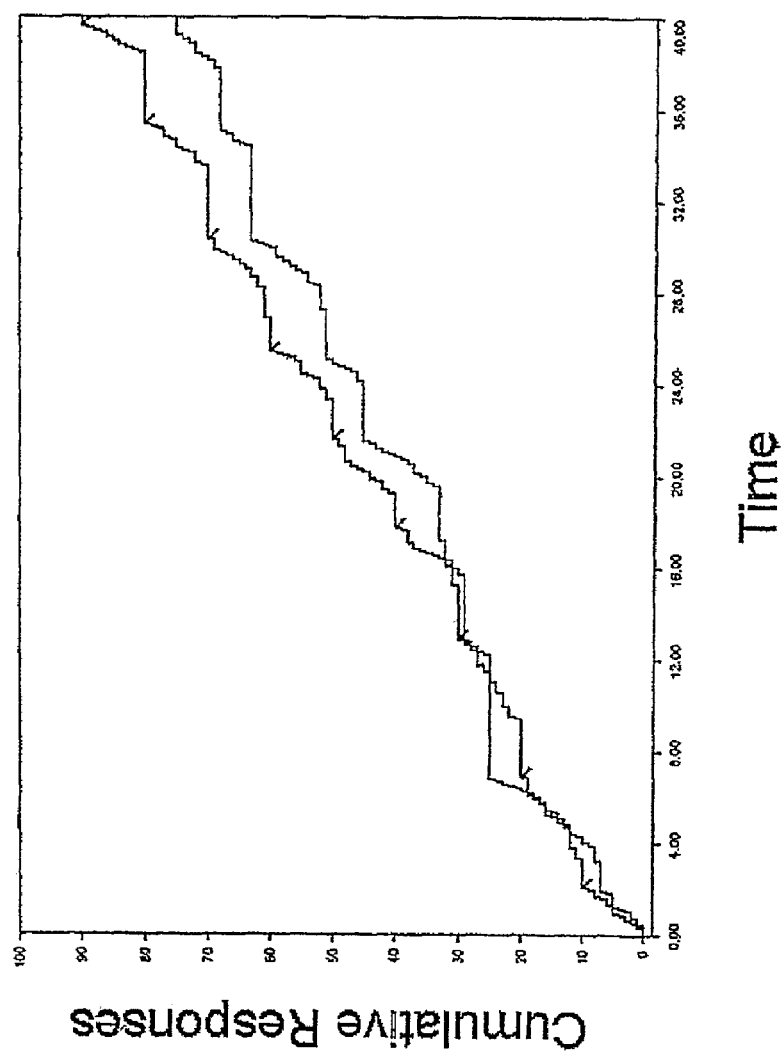
FIG. 4A illustrates a representative control performance measuring cumulative responses (both correct detections of a stimulus and errors) over time.

Model For Determining Increase in Attention. Rats were trained during daily sessions in a chamber which contained five holes along one wall. When a light came on behind one of the holes, the rat had 5 sec to respond by putting its nose in the hole. If it did this, a food pellet was dispensed. Lights came on for one second randomly in time. Each tenth "correct" response produced a food pellet. The rat had to continuously monitor (attend to) the lights to perform well. The results were measured and illustrated in FIG. 4A. The top curve shows the correct responses cumulatively throughout the session. The short diagonal marks on the line indicate the occasions on which food pellets were delivered. The bottom curve shows the incorrect responses cumulatively throughout a 40 min test session. As seen in FIG. 4A, without any sort of treatment, the number of incorrect responses was almost the same as the number of correct responses.

Figure 4B:
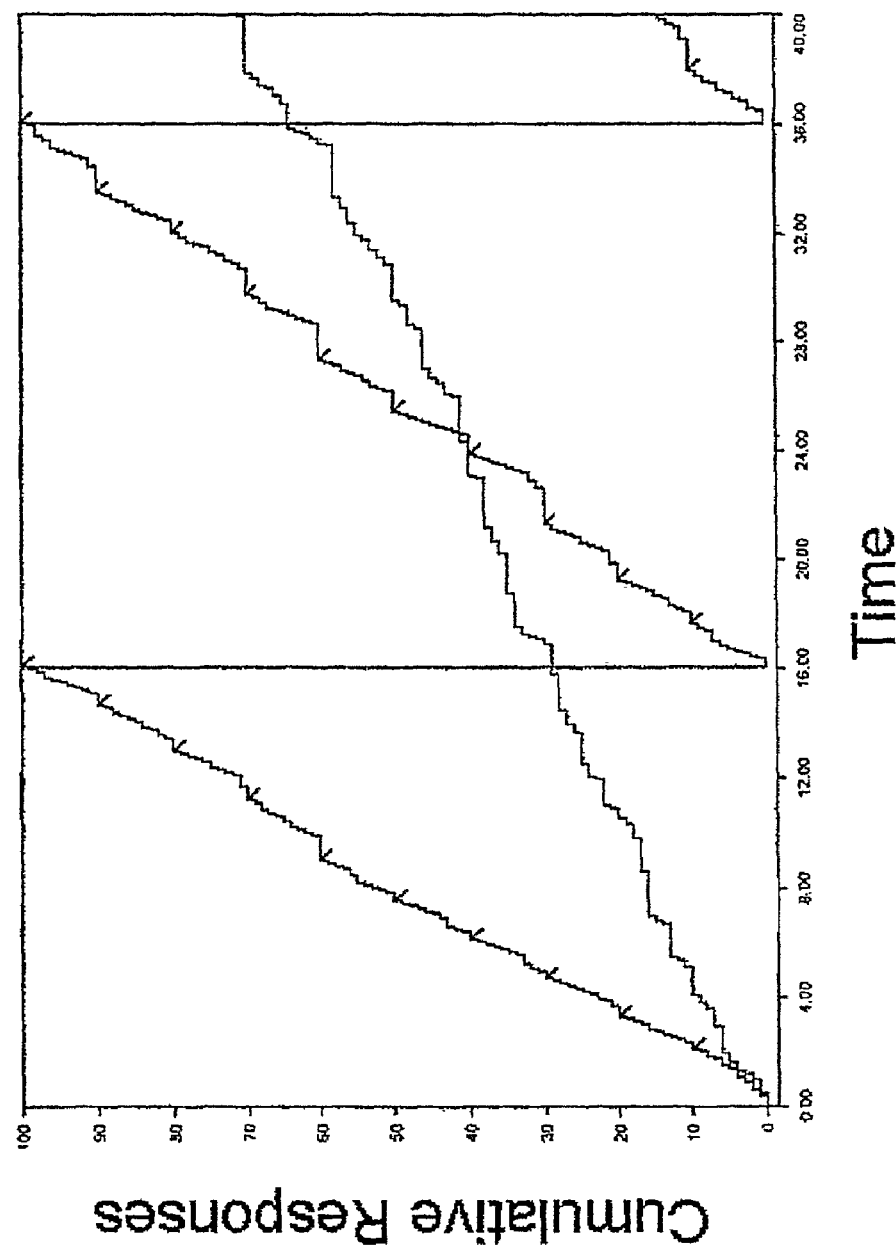
FIG. 4B illustrates the same performance after administration of a compound of formula III.

Rats were administered a dose of a compound of Formula III, in which $R^1$ is methyl and $R^2$ and $R^3$ are each fluoro. The same task was applied and the number of correct and incorrect responses was measured. The results are depicted in FIG. 4B. After administration of a compound of Formula III, the number of correct responses was far greater than before treatment and compared to the number of incorrect responses. These data represent an increase in the attention of the subject to the brief illuminations of lights relative to an untreated control.

Model For Reducing Effect of Nicotine. Food-deprived rats were trained to press one lever for a food pellet after nicotine administration and a second lever after vehicle administration. Pellets of food were delivered intermittently, so that every twentieth response produced food. Using this procedure, the only cue for the rat regarding which lever occasionally pays off with a food pellet, is the subjective effect of the nicotine. When the rats were accurately and reliably identifying the nicotine injections (approximately all of its responses on the lever that occasionally pays off after nicotine or saline), testing began. The rats were pretreated with a compound of Formula III before nicotine injection, and the experiment progressed as described above, except responses on either lever intermittently produced food. The data were measured and are depicted in Table 4. A 50% effective nicotine dose was reduced to low levels of effectiveness upon administration of a compound of Formula III.

TABLE 4

| Compound | Dose | Effect |
| --- | --- | --- |
| nicotine only (control) | | 50% |
| $R^1$ = Me<br>$R^2$, $R^3$ = F | 1.0 mg/kg | 7.65% |
| $R^1$ = allyl<br>$R^2$, $R^3$ = F | 3.0 mg/kg | 22.4% |
| $R^1$ = butyl<br>$R^2$, $R^3$ = F | 3.0 mg/kg | 2.67% |

Model For Reducing Food Intake. Rats had access to food and were allowed to eat as much as they could during a one hour period daily. Rats were administered a compound of Formula III at varying doses. The following compounds were tested:

| Code | Compound of Formula III |
| --- | --- |
| AHN 1-055 | $R^1$ = Me<br>$R^2$, $R^3$ = F |
| AHN 2-005 | $R^1$ = allyl<br>$R^2$, $R^3$ = F |
| JHW 007 | $R^1$ = butyl<br>$R^2$, $R^3$ = F |
| 4-Cl BZT | $R^1$ = Me<br>$R^2$ = Cl<br>$R^3$ = H |

| Code | Compound of Formula III |
|---|---|
| GBR 12909 (comparative) | 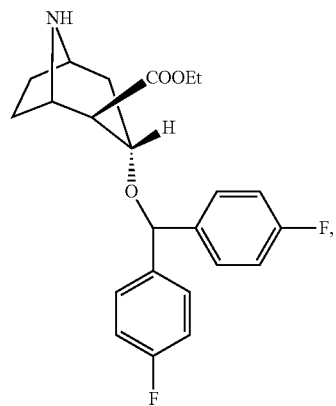 |

Figure 5:
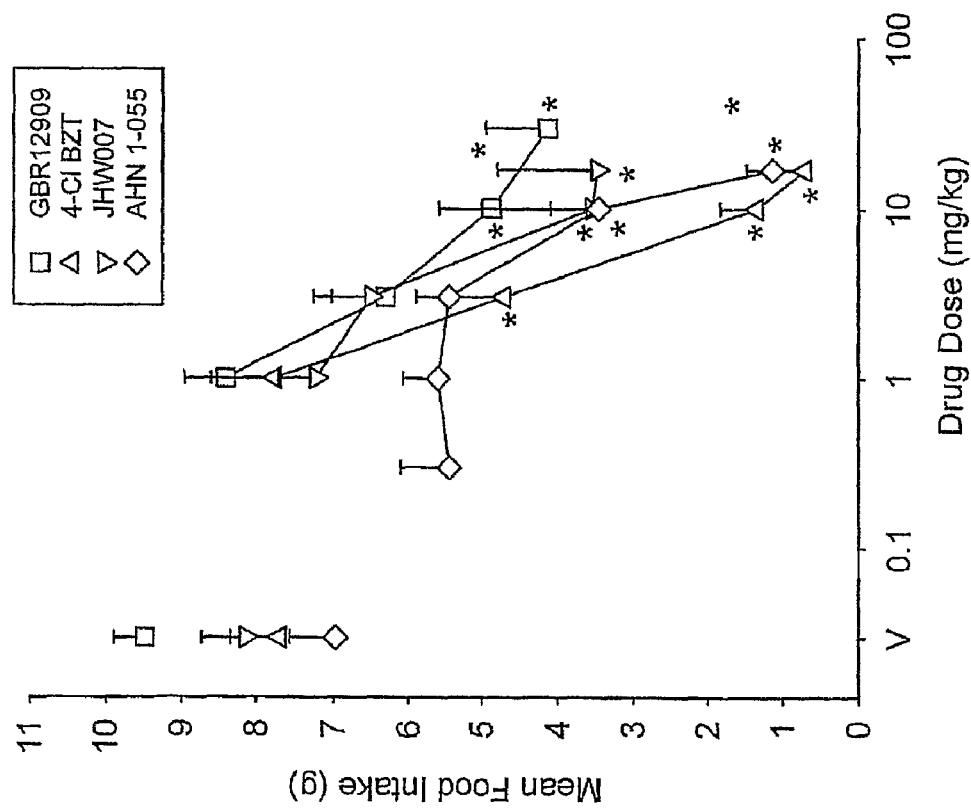
FIG. 5 illustrates reduction of food intake (g), after administration of compounds of formula III (mg/kg).

Known compound 1-(2-(bis(4-fluorophenyl)methoxy) ethyl)-4-(3-phenylpropyl)piperazine ("GBR 12909") was also tested. Increasing doses of a compound of Formula III decreased food consumption (FIG. 5).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound or salt thereof, wherein the compound is selected from the group consisting of

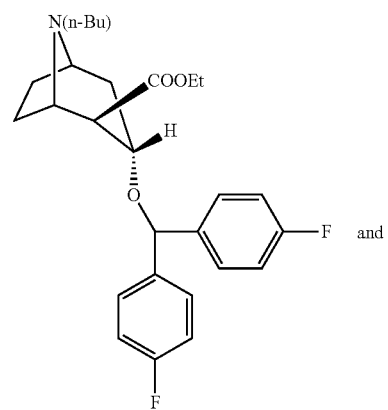

and

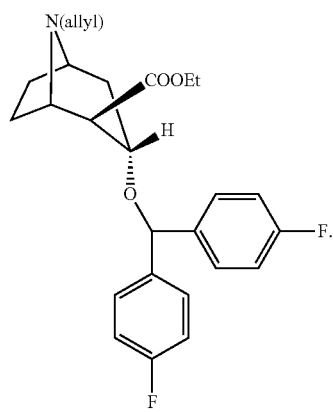
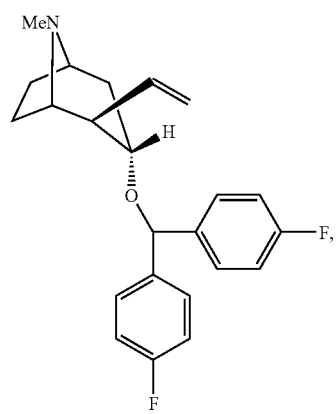
2. A compound or salt thereof, wherein the compound is selected from the group consisting of:
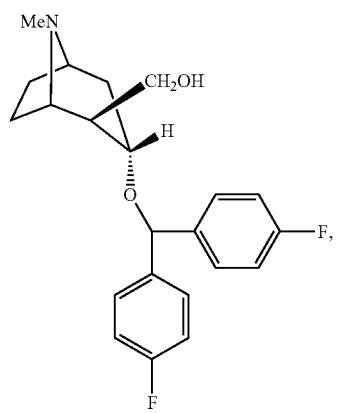
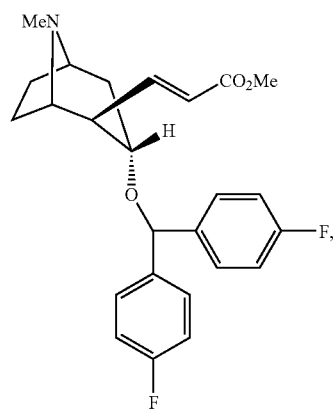
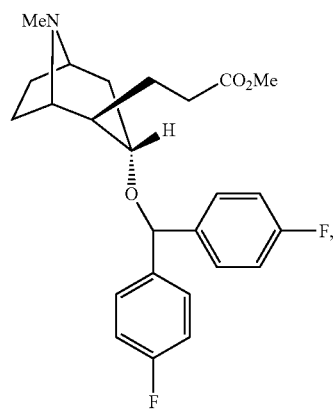
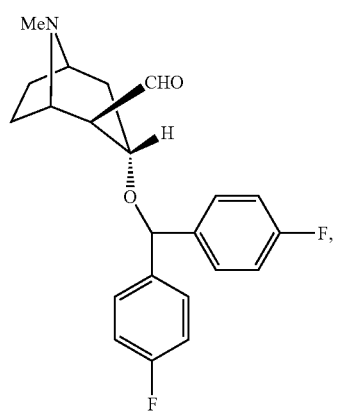
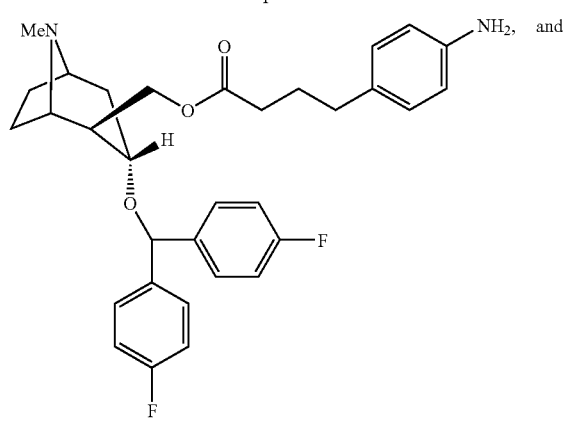

-continued

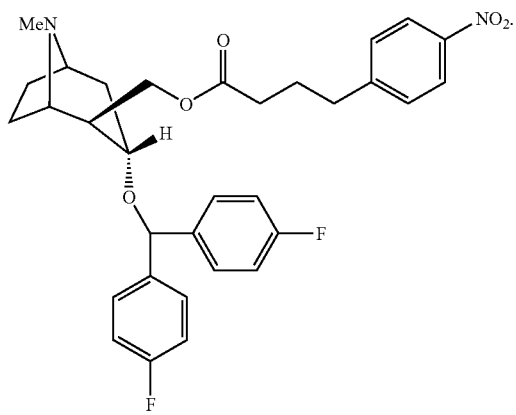

3. A pharmaceutical composition comprising a compound or salt of claim 1 and a pharmaceutically acceptable carrier.

4. A pharmaceutical composition comprising a compound or salt of claim 2 and a pharmaceutically acceptable carrier.

5. A compound or salt thereof, wherein the compound is

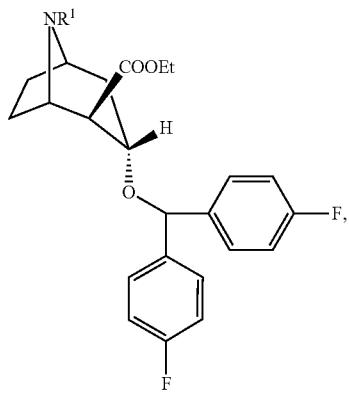

wherein $R^1$ is selected from the group consisting of $C_4$-$C_{12}$ alkyl, 2-aminoethyl, [2-(1H-indol-3-yl)-ethyl]-, and $C_1$-$C_{12}$ aminoalkyl.

6. A pharmaceutical composition comprising a compound or salt of claim 5 and a pharmaceutically acceptable carrier.

* * * * *